(12) United States Patent
Haag et al.

(10) Patent No.: US 9,102,595 B2
(45) Date of Patent: Aug. 11, 2015

(54) COMPOUNDS SUITED AS NANOCARRIERS FOR ACTIVE AGENTS AND THEIR USE

(75) Inventors: Rainer Haag, Berlin (DE); Wiebke Fischer, Berlin (DE); Mohiuddin Abdul Quadir, Berlin (DE); Ronit Satchi-Fainaro, Tel-Aviv (IL); Paula Ofek, Givataim (IL)

(73) Assignees: Ramot at Tel-Aviv University Ltd., Tel-Aviv (IL); Freie Universitaet Berlin, Berlin (DE)

( * ) Notice: Subject to any disclaimer, the term of this patent is extended or adjusted under 35 U.S.C. 154(b) by 1163 days.

(21) Appl. No.: 12/994,165

(22) PCT Filed: May 22, 2009

(86) PCT No.: PCT/EP2009/003803
§ 371 (c)(1), (2), (4) Date: Nov. 23, 2010

(87) PCT Pub. No.: WO2009/141170
PCT Pub. Date: Nov. 26, 2009

(65) Prior Publication Data
US 2011/0082090 A1   Apr. 7, 2011

(30) Foreign Application Priority Data
May 23, 2008 (EP) .................................. 08156816

(51) Int. Cl.
*A61K 38/00* (2006.01)
*C07C 271/20* (2006.01)
*C07C 217/28* (2006.01)

(52) U.S. Cl.
CPC ............. *C07C 271/20* (2013.01); *C07C 217/28* (2013.01)

(58) Field of Classification Search
CPC ................................ A61K 47/18; C07K 17/08
See application file for complete search history.

(56) References Cited

FOREIGN PATENT DOCUMENTS

WO   WO 2009/141170   11/2009

OTHER PUBLICATIONS

Tziveleka et. al. Synthesis and evaluation of functional hyperbranched polyether polyols as prospected gene carriers ,International Journal of Pharmaceutics 356 (2008) 314-324.*
Tziveleka et. al. Synthesis and Evolution of Functional Hyperbranched polyether polyols as prospected Gene Carriers. International Journal of Pharmaceutics. 356 (2008) 314-324.*
Jaszberenyi et. al. Physiochemical and MRI characterization of Gd3+-loaded polyamidoamine and hyperbranched dendrimers. J. Biol. Inorg. Chem. 12: 406-420, Jan. 10, 2007.*
International Preliminary Report on Patentability Dated Dec. 2, 2010 From the International Bureau of WIPO Re. Application No. PCT/EP2009/003803.
Communication Pursuant to Article 94(3) EPC Dated Mar. 23, 2012 From the European Patent Office Re. Application No. 09749660.8.
International Search Report Dated Jan. 15, 2010 From the International Searching Authority Re. Application No. PCT/EP2009/003803.
Ofek et al. "In Vivo Delivery of Small Interfering RNA to Tumors and Their Vasculature by Novel Dendritic Nanocarriers", The FASEB Journal, 24(9): 3122-3134, Sep. 2010.
Tziveleka et al. "Synthesis and Evaluation of Functional Hyperbranched Polyether Polyols as Prospected Gene Carriers", International Journal of Pharmaceutics, XP022625203, 356(1-2): 314-324, Jan. 16, 2008.

* cited by examiner

*Primary Examiner* — James H Alstrum Acevedo
*Assistant Examiner* — Jeanette Lieb

(57) ABSTRACT

The invention relates to a compound suited as entity carrier, having the general formula (I)

Figure 1:
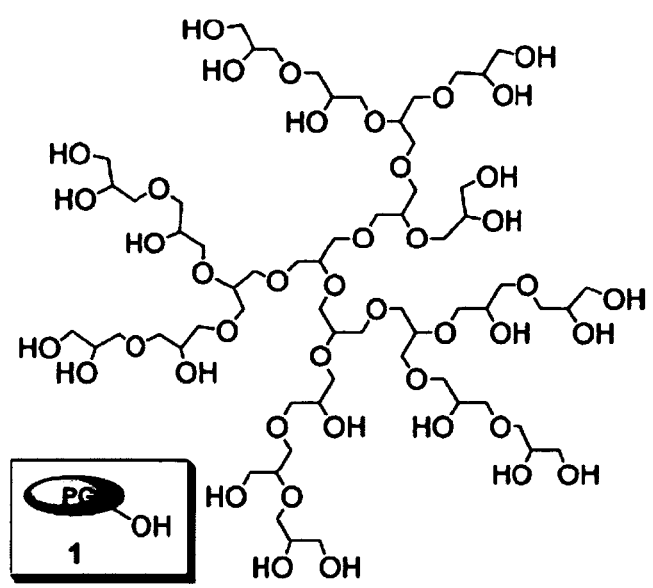

wherein X is an amine-containing residue further defined herein. The invention further relates to the use of such compounds, a nanocarrier system, a kit comprising such compounds and methods for gene silencing and anti-cancer treatment.

24 Claims, 17 Drawing Sheets

Putrescine

Spermidin

Spermin

Diethylenetriamine

Bis(3-aminopropylamine)

Pentaethylenhexaamine

A

B

COMPOUNDS SUITED AS NANOCARRIERS FOR ACTIVE AGENTS AND THEIR USE

RELATED APPLICATIONS

This Application is a National Phase of PCT Patent Application No. PCT/EP2009/003803 having International filing date of May 22, 2009, which claims the benefit of Europe Patent Application No. 08156816.4 filed on May 23, 2008. The contents of the above Applications are all incorporated herein by reference.

The invention relates to a nanocarrier system according to the preamble of claim 1, a compound being suited as entity carrier according to the preamble of claim 4, the uses of such a compound according to the preamble of claims 9 and 10, a kit comprising such a compound according to the preamble of claim 14 and application methods according to claims 15 and 17.

Gene therapy provides great opportunities for treating diseases like genetic disorders, infections, and cancer (T. G. Park et al. *Advanced Drug Delivery Reviews*, 2006, 58, 467-486). Double stranded RNA (dsRNA) induces sequence-specific post-transcriptional gene silencing by a process known as RNA interference (RNAi). The mediators of RNAi are small interference RNA (siRNA) segments of 21 to 25 base pairs in length.

These siRNAs bind to a ribonuclease complex called RNA-induced silencing complex (RISC) that guides the siRNA to its homologous mRNA targets. As a result, the bounded mRNA is cleaved; degradation of the mRNA results in gene silencing.

To achieve successful gene therapy, development of proper gene delivery systems is the main obstacle. For the uptake of DNA/siRNA various systemic and cellular barriers have to be circumvented.

A large variety of cationic compounds were reported to efficiently deliver nucleic acids or other biomolecules or even other substances such as metal ions into the cell. Generally, cationic compounds are needed to carry nucleic acids into a cell since the latter show an overall negative charge (due to their phosphate backbone) so that a charge interaction between the carrier and the nucleic acid to be carried can occur.

One of the most powerful and versatile families of carriers are polyamines. However, these polyamines exert rather high cell toxicity and low biocompatibility. Therefore, polyamines are not well suited as carriers for in vivo applications.

Cationic lipids, such as the HiPerFect reagent of Qiagen, Hilden, Germany, are also used as carrier compounds. In this context, HiPerFect is the benchmark reagent for in vitro transfections. However, due to its cell toxicity, it is not well suited as siRNA carrier for in vivo applications.

Other siRNA carriers include the RNAiFect reagent (Qiagen), DOTAP (Roche), lipofectamine (Gibco) and polyethylene imine. All compounds show also significant cell toxicity and are thus only suited for in vitro applications.

Roller et al. (S. Roller, H. Zhou, R. Haag, *Molecular Diversity*, 2005, 9, 305-316) describe different amine-substituted polyglycerol-based polymeric scaffolds. However, no use of these compounds as carriers has been proposed hitherto. In addition, N-Benzyl-O-polyglyceryl carbamate described by Roller et al. is not at all suited as carrier since it is too hydrophobic and is not water soluble.

Tziveleka et al. (L.-A. Tziveleka, A.-M. G. Psarra, D. Tsiourvas, C. M. Paleos, International Journal of Pharamceutics, 2008, 356, 314-324) describe five derivatives of hyperbranched polyether polyols being functonalized with quarternary or tertiary ammonium groups. These derivatives may be used to carry plasmidic DNA (pDNA).

For a transfection to be therapeutically successful, it is imperative that polymeric scaffolds to be used as carriers exert reduced cell toxicity and higher biocompatibility.

It is an objective of the invention to provide novel compounds being suited as carriers for diverse substances, also in vivo, as well as to provide a nanocarrier system and to provide a novel use of already known compounds.

This objective is attained by a nanocarrier system according to claim 1. Such a nanocarrier system comprises at least one nanocarrier being a compound having a structure according to formula (I),

wherein PG denotes a linear or branched polyglycerol core, and
X being

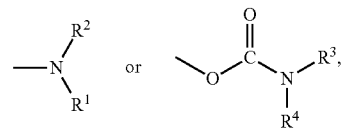

preferably

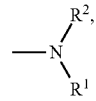

and being covalently bound to a carbon atom of the polyglycerol core, wherein the polyglycerol core carries a plurality of groups of the type X, $R^1$ being H, linear or branched $C_1$-$C_{10}$-Alkyl, which may be substituted and/or interrupted by one or more oxygen, sulphur and/or nitrogen atoms, or $R^3$, $R^2$ being H, linear or branched $C_1$-$C_{10}$-Alkyl, which may be substituted and/or interrupted by one or more oxygen, sulphur and/or nitrogen atoms, or $R^3$, $R^3$ being

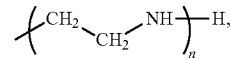

$R^4$ being H or $C_1$-$C_4$-Alkyl, which may be substituted and/or interrupted by one or more oxygen, sulphur and/or nitrogen atoms, and n being 1 to 100.

The nanocarrier system further comprises at least one entity to be carried by and bound to said nanocarrier in a covalent, ionic or complexed manner, wherein said entity is chosen from the group comprising nucleotides, nucleosides, linear or circular single or double stranded oligonucleotides, oligomeric molecules comprising at least one nucleoside, small pharmacologically active molecules having a molecular mass of not more than 800 g/mol, amino acids, peptides, and metal ions.

In this context, the entity of the claimed nanocarrier system does preferably not comprise double stranded circular and covalently closed nucleic acid species (preferably DNA or RNA, in particular DNA) having a length of more than 1000 bases or base pairs, preferably of more than 500 bases or base pairs. Thus, plasmidic DNA, i.e. double stranded circular and covalently closed DNA having more than 1000 base pairs or more than 500 base pairs preferably cannot be part of the nanocarrier system. However, in certain embodiments, it is possible that the entity may also be plasmidic DNA according to the definition given above.

In an embodiment, the entity of the nanocarrier system is a ribonucleic oligonucleotide, i.e. an RNA oligonucleotide. In another embodiment, the ribonucleic oligonucleotide is a messenger RNA (mRNA) or an mRNA analogue, a micro RNA (miRNA), a small interfering RNA (siRNA) or a tiny noncoding RNA (tnRNA).

In another embodiment, the oligonucleotide is a double stranded circular covalently closed deoxyribonucleic or ribonucleic oligonucleotide with a length of ca. 20 to less than 1000 base pairs, preferably of ca. 20 to less than 500 base pairs.

In another embodiment, the ribonucleic oligonucleotide has a length of 8 to 50 bases, preferably 10 to 40 bases, preferably 10 to 30 bases, preferably 12 to 25 bases, preferably 12 to 22 bases.

In any case, the bases which might be part of the nucleotides, nucleosides, or oligonucleotides used as or in the entity of the nanocarrier system, can be natural or non-natural bases. E.g., suited nucleoside analogues include, but are not limited to inosine, nebularine, nitropyrrole, nitroindole, 2-aminopurine, 2,6-diaminopurine, locked nucleic acids (LNAs) nucleosides, peptide nucleic acids (PNAs) nucleosides, purine, hypoxanthine, xanthine, ethanocytosin, 5-methylcytosine, 5-alkynylcytosine, 2,6-diaminopyrimidino, 2,6-diaminopyrazine, 5-fluorouracil, 5-bromouracil, 5-chlorouracil, 5-iodouracil, pseudoisocytosine, 2-hydroxy-5-methyl-4-triazolopyridin, isocytosine, isoguanine, inosine, 4-acetylcytosine, dihydrouracil, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, 5-methoxyuracil, 2-methylthio-N6-isopentenyladenine, pseudouracil, queosine, 2-thiocytosine, 5-methyl-2-thiouracil, 2-thiouracil, 4-thiouracil, 5-methyluracil, uracil-5-oxyacetic acid methylester, 5-methyl-2-thiouracil, 3-(3-amino-3-N-2-carboxypropyl), pseudouridine, pseudocytosine, pseudoisocytosine, 5-propynylcytosine, isocytosine, isoguanine, 2-thiopyrimidine, 6-thioguanine, 4-thiothymine, 4-thiouracil, $O^6$-methylguanine, $N^6$-methyladenine, $O^4$-methylthymine, 5,6-dihydrothymine, 5,6-dihydrouracil, 4-methyl-indole, and ethenoadenine.

Accordingly, the nucleotides can be modified in this manner. The oligonucleotides may be LNAs or PNAs. PNA is a polymer of purine and pyrimidine bases which are connected to each other via a 2-amino ethyl bridge. PNA binds sequence specifically with high affinity to an according DNA or RNA complement. In LNA, the 2'-hydroxyloxygen of ribose is connected to the C-4 atom of the same ribose unit via a methylene bridge. The conformational restriction of LNA compared to RNA or DNA apparently leads to a higher binding affinity.

All possible meanings for the entity as defined above are to be understood as individually disclosed herein and to be optionally combined in any desired manner.

In an embodiment, the nanocarrier system comprises a polyglycerol core in which at least 50%, particularly at least 60%, particularly at least 70%, particularly at least 80%, particularly at least 90%, particularly at least 95%, particularly at least 99%, particularly all of the free hydroxyl groups of the polyglycerol core are substituted by groups of the type X.

In another embodiment, n is preferably 1 to 10, particularly 5.

In another embodiment, the nanocarrier system preferably comprises a compound in which $R^1$ is a methyl residue and $R^2$ is an N-dimethyl ethyl amine residue.

The objective is also attained by a compound having the features of claim 1. Such a compound is suited as entity carrier and has the general formula (I)

(I)

with
PG denoting a linear or branched polyglycerol core,
X being

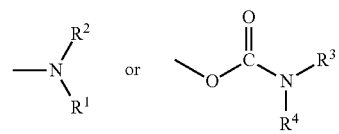

and being covalently bound to a carbon atom of the polyglycerol core, wherein the polyglycerol core carries a plurality of groups of the type X, $R^1$ being H, linear or branched $C_1$-$C_{10}$-Alkyl, which may be substituted and/or interrupted by one or more oxygen, sulphur and/or nitrogen atoms, or $R^3$, $R^{2'}$ being linear or branched $C_1$-$C_{10}$-Alkyl, which may be substituted and/or interrupted by one or more oxygen, sulphur and/or nitrogen atoms, or $R^3$, $R^3$ being

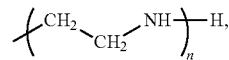

$R^4$ being H or $C_1$-$C_4$-Alkyl, which may be substituted and/or interrupted by one or more oxygen, sulphur and/or nitrogen atoms, and n being 1 to 100,
wherein $R^1$ and $R^{2'}$ cannot simultaneously be an ethyl residue.

In an embodiment, the entity to be carried by said compound suited as entity carrier is chosen from the group comprising nucleotides, nucleosides, linear or circular single or double stranded oligonucleotides, oligomeric molecules comprising at least one nucleoside, small pharmacologically active molecules having a molecular mass of not more than 800 g/mol, amino acids, peptides, and metal ions. In an embodiment, the afore-mentioned group does not comprise DNA or plasmidic DNA or essentially completely double stranded nucleic acids or any combination thereof.

E.g., a single nucleoside (of ribonucleic acid or of deoxyribonucleic acid) like uridine or deoxythymidine or a plurality of identical or different nucleosides may serve as entity. Examples of nucleotides are adenosine monophosphate (AMP), adenosine diphosphate (ADP) and adenosine triphosphate (ATP). Also, different metal ions, particularly cations such as $Ag^+$, $Ca^{2+}$, $Cu^{2+}$ or $Mg^{2+}$ ions, or aptamers of peptides or oligonucleotides may serve as entity. In case of the entity being metal ions, preferably a non-covalent, complexed form of interaction between the metal ions and the carrier is established.

Another example of a suited entity are single or double stranded RNA or DNA oligomers of, e.g., 20 to 25 base pairs or bases, respectively, in length. Double stranded RNA is particularly suited. Thus, the compound may also serve as siRNA carrier. Another example of suited entities are chimeric molecules of amino acid residues and nucleosides or nucleotides.

Reference is also made to the explanations given above with respect to the nanocarrier system which are also applicable for the compound and its use.

All possible meanings for the entity as defined above are to be understood as individually disclosed herein and to be optionally combined in any desired manner.

As can be seen from formula (I) and the residue definitions given above, the claimed compound has a polyglycerol (PG) based gene-transfection motif with core-shell architecture. The shells of such motifs can be tailored to contain amines with different numbers of cationic sites for mimicking the activity of polyamines. Since the compounds are based on a PG structure, they provide appreciable clinical compliance.

In contrast to polyamines and other known compounds used as carriers, the novel compounds carry charges at physiological pH only on their surface or shell (namely on nitrogen atoms located on the surface or being part of the shell), whereas the core is comprised of short alkyl chains connected via ether bridges to each other being substantially not charged. The polyglycerol core may be structured in a linear or branched manner. In an embodiment, the structure of the polyglycerol is at least partially branched.

The shell of the polyglycerol-based compounds may have a layered structure due to a repetitive nitrogen-containing motif. E.g., by use of a pentaethylenehexamine residue as shell (as is the case in polyglyceryl pentaethylenehexamine carbamate), a five-fold layered shell is achieved.

The polyglycerol base material can be obtained in a kilogram scale which contains linear monohydroxy and terminal dihydroxy functionalities which can be modified selectively as linkers for diverse organic synthesis.

The polyglycerol core of the claimed compounds is biocompatible. However, by introducing nitrogen-containing shell motifs, the cell toxicity of the compounds is raised. Thus, when designing carriers to be especially used for in vivo applications, care must be taken to keep the cell toxicity of the complete compound at a low level. On the other hand, the transfection efficacy should be as high as possible. Consequently, a balance must be found between toxicity and transfection efficacy. Regarding the claimed compounds, such a balance is established.

Specific, symmetric polyglycerol dendrimers are an example of polyglycerol which can be used for the polyglycerol core of the nanocarrier system or the compound. These dendrimers are highly symmetric. They are generated from smaller molecules by repeated reaction steps, wherein always higher degrees of branching result. At the end of the branches, functional groups are located which are the starting point for further branchings. Thus, with each reaction step, the number of monomeric end groups increases exponentially, leading to a hemicircular tree structure.

In this context, the term "polyglycerol" as used herein includes any substance which contains at least two glycerol units in its molecule and wherein said molecule is characterized by a branched structure. According to the present invention, the term "glycerol unit" does not only relate to glycerol itself but also includes any subunits which are based on glycerol, such as for example:

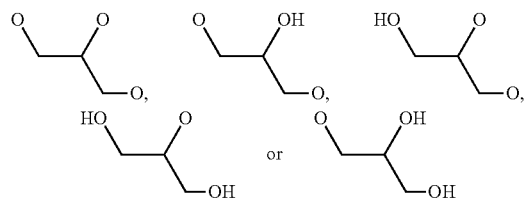

Preferably, the polyglycerol includes three or more, preferably ten or more, and particularly 15 or more of said glycerol units. The polyglycerol structure can be obtained, e.g., by a perfect dendrimer synthesis, a hyperbranched polymer synthesis or a combination of both and is per se known to a person skilled in the art.

In an alternative embodiment, at least 50%, particularly at least 60%, particularly at least 70%, particularly at least 80%, particularly at least 90%, particularly at least 95%, particularly at least 99%, particularly all of the free hydroxyl groups of the polyglycerol core of the compound are substituted by groups of the type X. The rate of substitution is also referred to as conversion. Thus, if a conversion of 100% is achieved during synthesis, the starting material polyglycerol of the formula $PG\text{-}(OH)_p$ was reacted to $PG\text{-}(X)_m$ with m=p. If, e.g., a product of the formula $(X)_m\text{-}PG\text{-}(OH)_q$ with m=0.8*n and q=0.2*p is obtained, the conversion is 80%.

As an alternative, n is 1 to 10, particularly 2 to 8, particularly 3 to 6 and in particular 5. As another alternative, $R^4$ is H. If X is

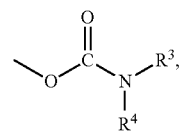

n is 5 and $R^4$ is H, the compound would be polyglyceryl pentaethylenehexamine carbamate.

In another embodiment, $R^1$ is a methyl residue and $R^{2'}$ is an N-dimethyl ethyl amine residue so that an N,N,N'-trimethyl-ethylenediamine residue is bound to the polyglycerol core structure via one of its nitrogen atoms.

The objective is also achieved by a use of a compound as defined above (with all alternative embodiments) with respect to the claimed compound or of a compound according to general formula (I), wherein X is

according to claim 9. This use is directed to the preparation of a pharmaceutical composition, wherein the compound acts as carrier for an entity, wherein the entity is chosen from the group comprising nucleotides, nucleosides, linear or circular single or double stranded oligonucleotides, oligomeric molecules comprising at least one nucleoside, small pharmacologically active molecules having a molecular mass of not more than 800 g/mol, amino acids, peptides, and metal ions. However, it is mandatory that the entity does not comprise a double stranded circular and covalently closed nucleic acid (preferably DNA or RNA, in particular DNA) having a length of more than 1000 bases or base pairs, preferably of more than 500 bases or base pairs.

Examples of entities are disclosed above. All possible meanings for the entity as defined above are also in the context of the claimed uses to be understood as individually disclosed herein and to be optionally combined in any desired manner.

The pharmaceutical composition may be used to treat diverse diseases, such as diseases which are amenable to treating by gene silencing like, e.g., certain types of cancer. Further, in particular when $Cu^{2+}$ ions are used as entity, the pharmaceutical composition may serve for slowing down aging.

The objective is also achieved by the use of a compound of the general formula (I) as explained above (with all alternative embodiments) with respect to the claimed compound or of a compound according to general formula (I), wherein X is

as entity carrier for in vitro, in vivo, ex vivo or in situ applications.

In this context, the entity is chosen from the group comprising nucleotides, nucleosides, linear or circular single or double stranded oligonucleotides, oligomeric molecules comprising at least one nucleoside, small pharmacologically active molecules having a molecular mass of not more than 800 g/mol, amino acids, peptides, and metal ions. However, at least in case of $R^1$ and $R^2$ both being an ethyl residue, the entity does not comprise a double stranded circular and covalently closed nucleic acid (preferably DNA or RNA, in particular DNA) having a length of more than 1000 bases or base pairs, preferably of more than 500 bases or base pairs. If the polyglycerol core is substituted by a carbamate residue or a residue of the general structure

plasmidic nucleic acids (i.e. double stranded circular and covalently closed nucleic acids) are also suited as entity in an embodiment.

In an alternative embodiment, the use is directed only to in vitro, ex vivo or in situ applications, but not to in vivo applications. In another alternative embodiment, the use is directed only to in vitro or ex vivo applications, but not to in vivo or in situ applications.

In another embodiment, it is preferred to use the entity carrier for in vivo or in situ applications.

An example of such a use or a use as pharmaceutical composition is to utilize the entity carrier to transport said entity into at least one prokaryotic or eukaryotic cell, in particular into at least one human or animal cell. Transporting said entity in a plurality of entity carriers into a plurality of cells is preferred. Suited animal cells are, e.g., cells of mammals like, e.g., rodents such as rats or mice.

In an alternative embodiment, the entity carrier is used to transport entity into at least one animal cell but not into a human cell. Thus, the use of the compound as entity carrier may be defined as for in vitro, in vivo, ex vivo or in situ applications with respect to animal cells and for in vitro, ex vivo or in situ applications for human cells.

In an embodiment, the use is directed to silence a gene within a cell, preferably a tumor gene, by a ribonucleic acid, such as siRNA.

In another embodiment, the entity carrier bears at least one functional group of the general formula

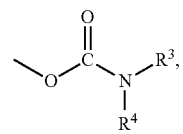

wherein residues $R^3$ and $R^4$ have the above-defined meanings, and in that said functional group is cleaved from the polyglycerol core of the entity carrier once the entity carrier is located within its target cell. This cleavage results in an even better biocompatibility of the compound, since potentially cytotoxic amine structures of the compound like polyamine or polyethyleneamine structures are separated from the generally biocompatible polyglycerol core structure.

In another embodiment, said cleavage is performed by an enzyme. E.g., the compound may be designed in such a way that an esterase or a carbamate hydrolase may cleave the carbamate bond so that the polyglyceryl core is separated from the surrounding amine-containing surface or shell.

Again, all possible meanings for the entity as defined above are also in the context of the claimed nanocarrier system to be understood as individually disclosed herein and to be optionally combined in any desired manner.

The invention also relates to a kit for performing transfection reactions, comprising a compound of general formula (I) as defined above in any suited formulation. E.g., a formulation as a solution in a phosphate buffered saline (PBS) at pH 7.4 or as a lyophilized product with or without adducts may be suited. Other buffer systems can also be used.

The object is also achieved by a method for silencing a gene in vitro, ex vivo, in situ or in vivo according to claim 15. This method is characterized by applying a nanocarrier system as described above or a compound as described above together with at least one entity to be carried by and bound to the mentioned compound in a covalent, ionic or complexed manner into at least one human or animal cell. Thereby, the entity is a ribonucleic oligonucleotide.

In an alternative embodiment, the method is directed only to in vitro or ex vivo applications, but not to in vivo or in situ applications. In another alternative embodiment, the method is directed only to in vitro, in situ or ex vivo applications, but not to in vivo applications.

The application of the nanocarrier system or the compound/ribonucleic acid is done such that the ribonucleic acid can interact with mRNA being present in said cell.

In another embodiment, it is preferred to use the method for in vivo or in situ applications.

In an embodiment, the gene to be silenced is a tumor related gene.

The object is further achieved by a method for the treatment of cancer according to claim 17. This method is characterized by administering a nanocarrier system as described above or a compound as described above together with at least one entity to be carried by and bound to said compound in a covalent, ionic or complexed manner, to at least one human or animal being. Thereby, the entity is chosen from the group comprising nucleotides, nucleosides, linear or circular single or double stranded oligonucleotides, oligomeric molecules comprising at least one nucleoside, small pharmacologically active molecules having a molecular mass of not more than 800 g/mol, amino acids, peptides, and metal ions In an embodiment, the treatment of cancer is performed as combination treatment by a combined administering of the nanocarrier system or the compound/entity according to the invention together with a known anti-cancer or an anti-angiogenic drug. Exemplary cytotoxic agents suited as anti-cancer drug include, without limitation, anthracycline antibiotics like doxorubicin and daunorubicin; taxanes like paclitaxel Taxol™, docetaxel; vinca alkaloids like vincristine and vinblastine, anti-metabolites like methotrexate, 5-fluorouracil (5 FU), leucovorin, irinotecan, idarubicin, mitomycin C, oxaliplatin, raltitrexed, tamoxifen and cisplatin, carboplatin, actinomycin D, mitoxantrone or blenoxane or mithramycin.

Exemplary anti-angiogenic drugs include, but are not limited to: (1) monoclonal antibodies directed against specific proangiogenic factors and/or their receptors; (avastin, erbitux, vectibix, herceptin) and (2) small molecule tyrosine kinase inhibitors (TKIs) of multiple proangiogenic growth factor receptors (tarceva, nexavar, sutent, iressa). Inhibitors of mTOR (mammalian target of rapamycin) represent a third, smaller category of antiangiogenic therapies with one currently approved agent (torisel). In addition, at least two other approved anti-angiogenic agents may indirectly inhibit angiogenesis through mechanisms that are not completely understood (velcade, thalidomide/celgene). Other anti-angiogenic agents that are suitable for use in the context of embodiments of the invention include, but are not limited to, paclitaxel, 2-methoxyestradiol, prinomastat, batimastat, BAY 12-9566, carboxyamidotriazole, CC-1088, dextromethorphan acetic acid, dimethylxanthenone acetic acid, endostatin, IM-862, marimastat, a matrix metalloproteinase, penicillamine, PTK787/ZK 222584, RPI.4610, squalamine lactate, SU5416, thalidomide, combretastatin, tamoxifen, COL-3, neovastat, BMS-275291, SU6668, anti-VEGF antibody, medi-522 (vitaxin II), CAI, interleukin-12, IM862, amilloride, Angiostatin®protein, angiostatin K1-3, angiostatin K1-5, captopril, DL-alpha-difluoromethylornithine, DL-alpha-difluoromethylornithine HCl, His-Tag® Endostatin™ protein, Endostar™, fumagillin, herbimycin A, 4-Hydroxyphenylretinamide, juglone, laminin, laminin hexapeptide, laminin pentapeptide, lavendustin A, medroxyprogesterone, medroxyprogesterone acetate, minocycline, minocycline HCl, placental ribonuclease inhibitor, suramin, sodium salt suramin, human platelet thrombospondin, neutrophil granulocyte; interferon alpha, beta and gamma; IL-12; matrix metalloproteinases (MMP) inhibitors (e.g. COL3, Marimastat, batimastat); EMD121974 (cilengitide); ZD6474, SU11248, Vitaxin; squalamin; COX-2 inhibitors; PDGFR inhibitors (e.g., gleevec); NM3 and 2-ME2.

Alternative embodiments of the nanocarrier system, the compound or the entity as indicated above are also independently applicable for the claimed methods.

The invention will be explained in the following with reference to figures and examples. This will be done for better understanding of the invention is not intended to limit the scope of protection in any way.

Figure 2:
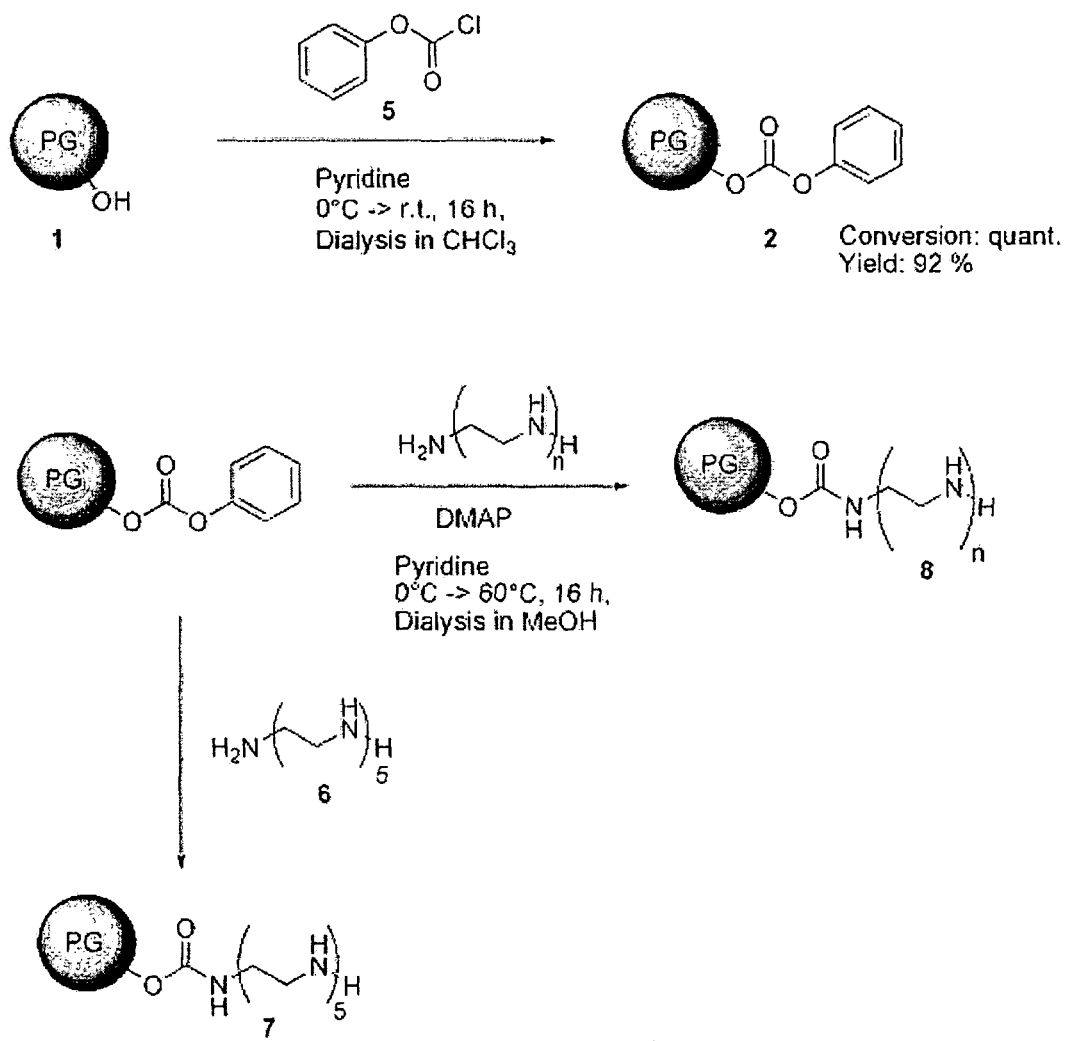
Figure 3:
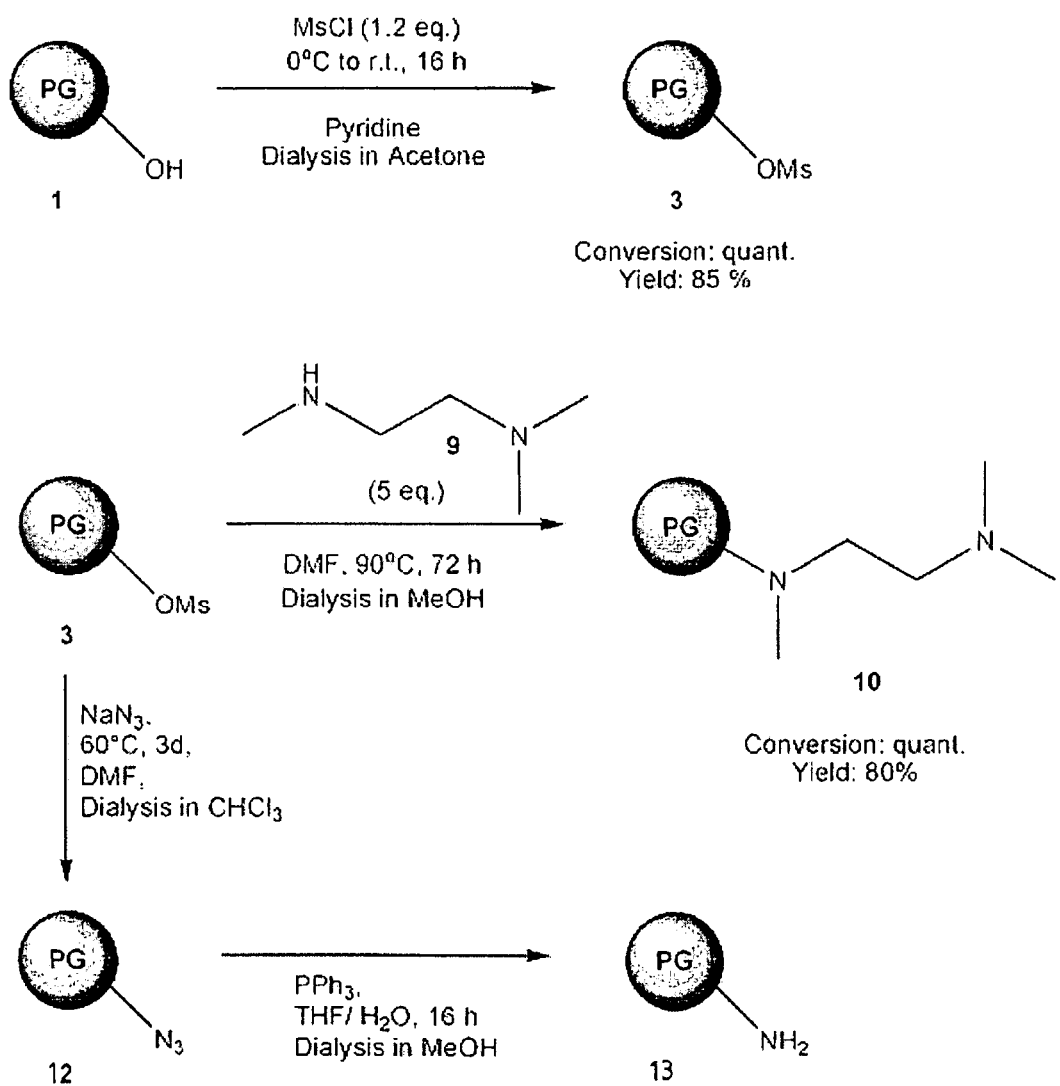
Figure 4:
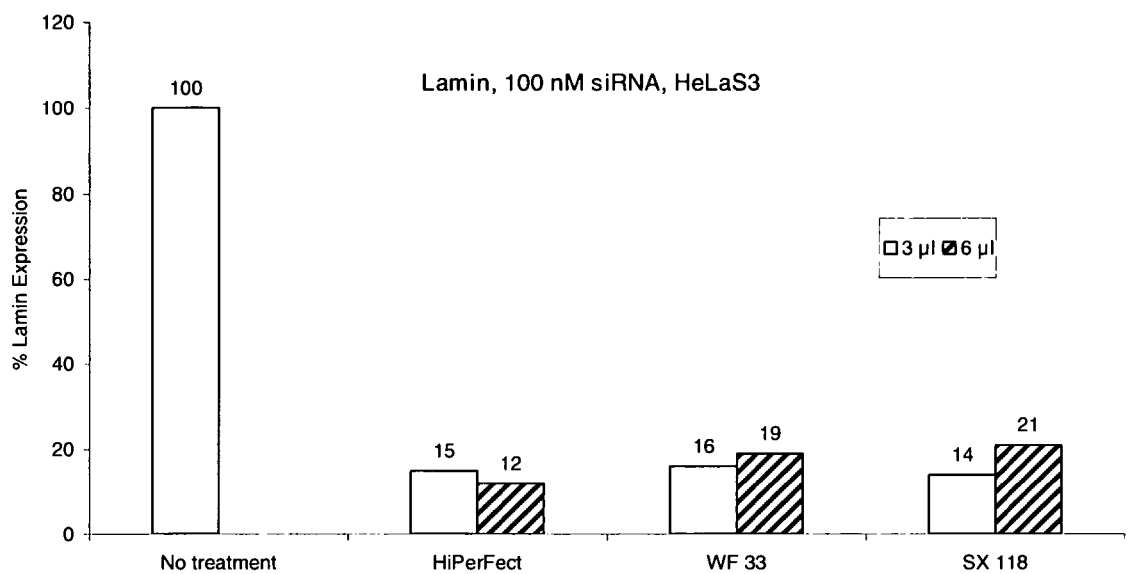
Figure 5:
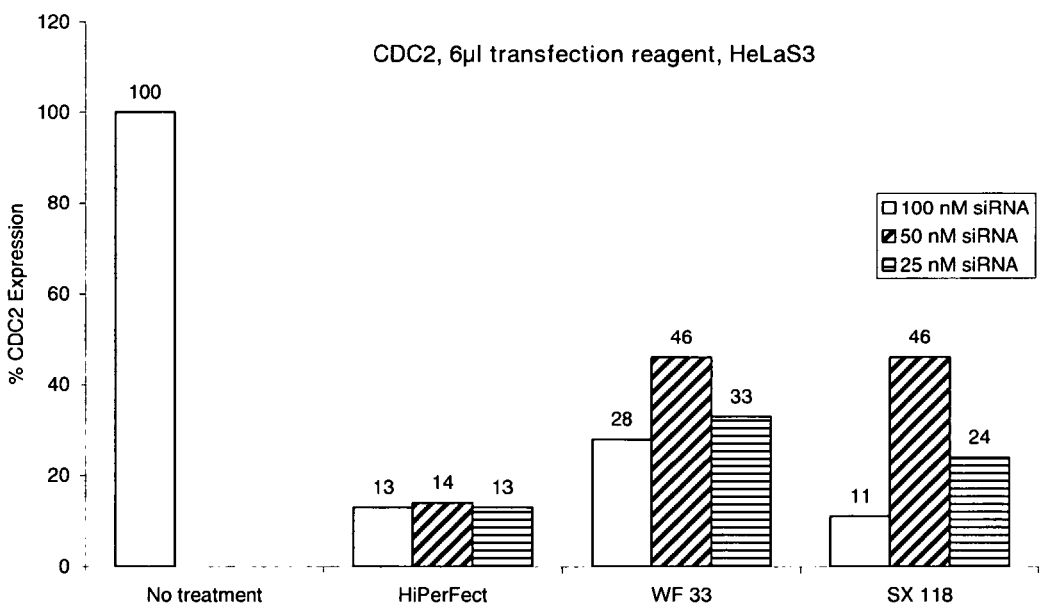
Figure 6:
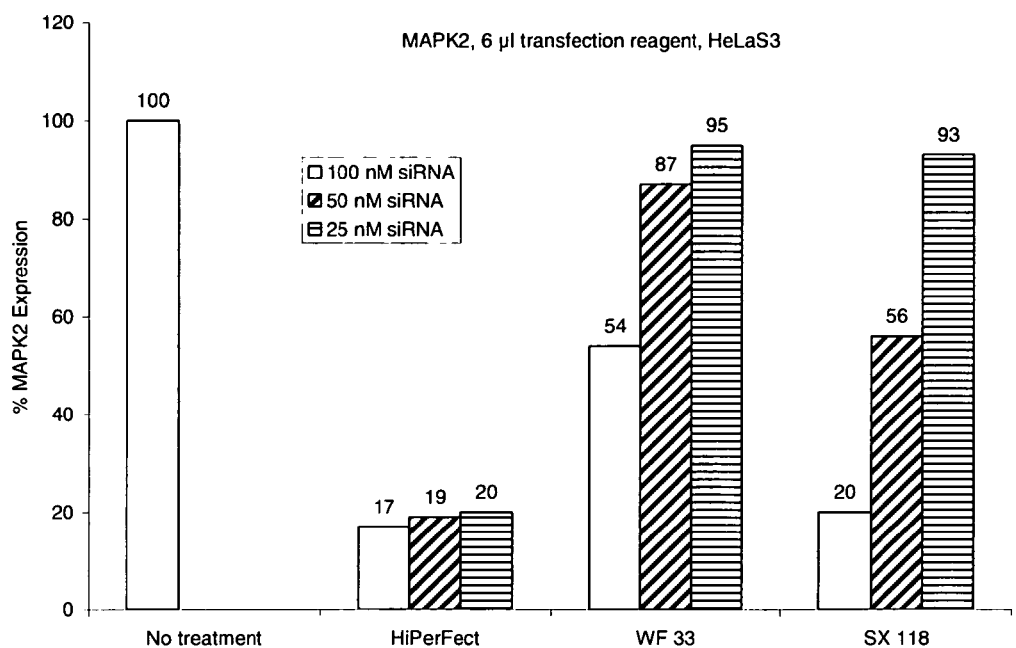
Figure 7:
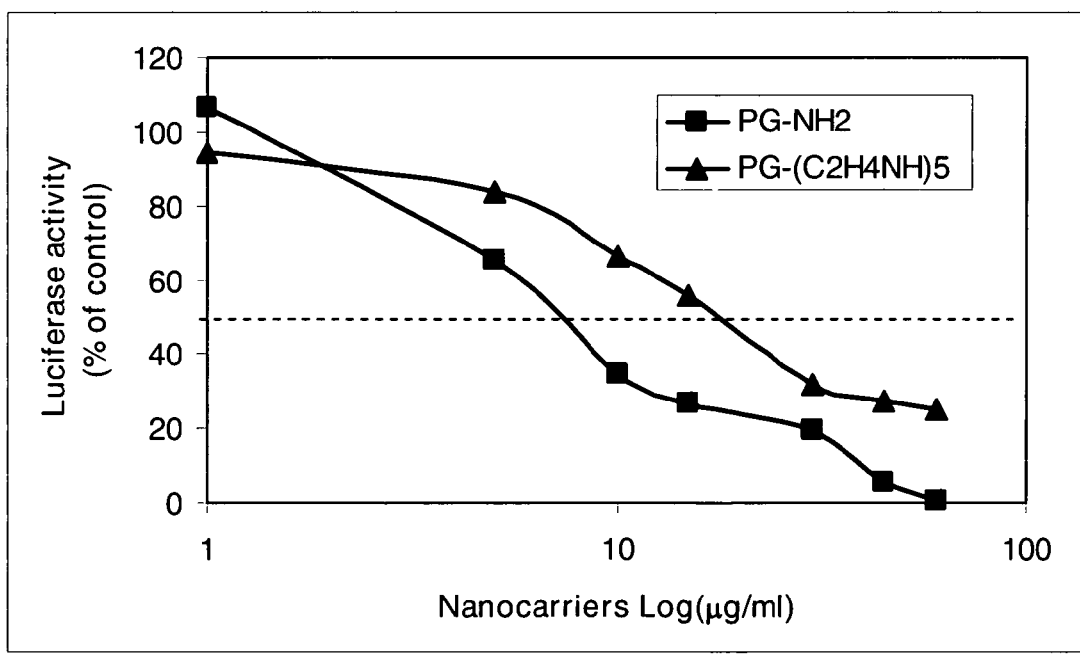
Figure 8:
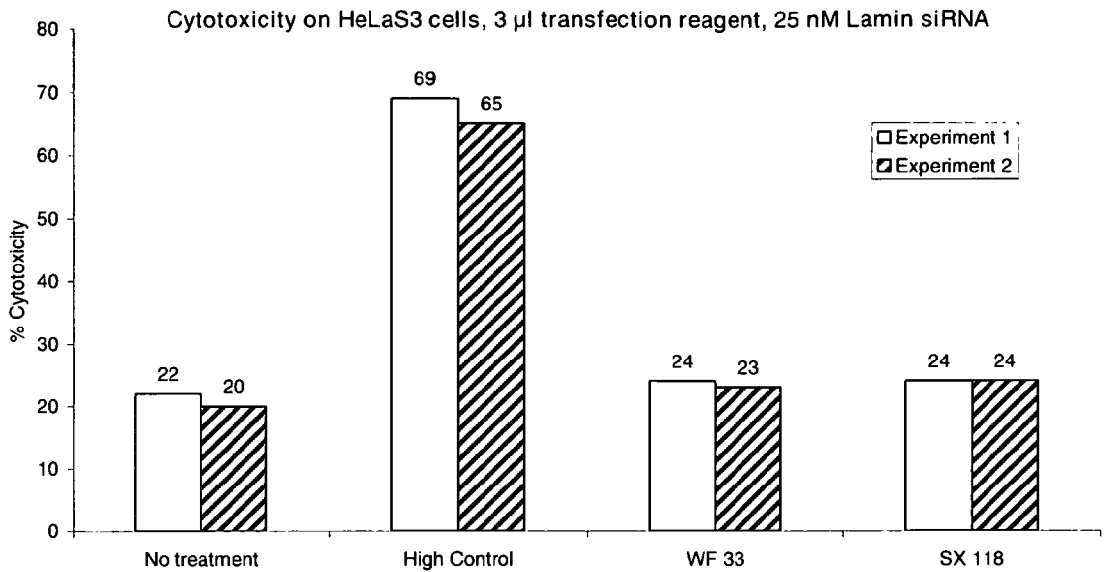
Figure 9:
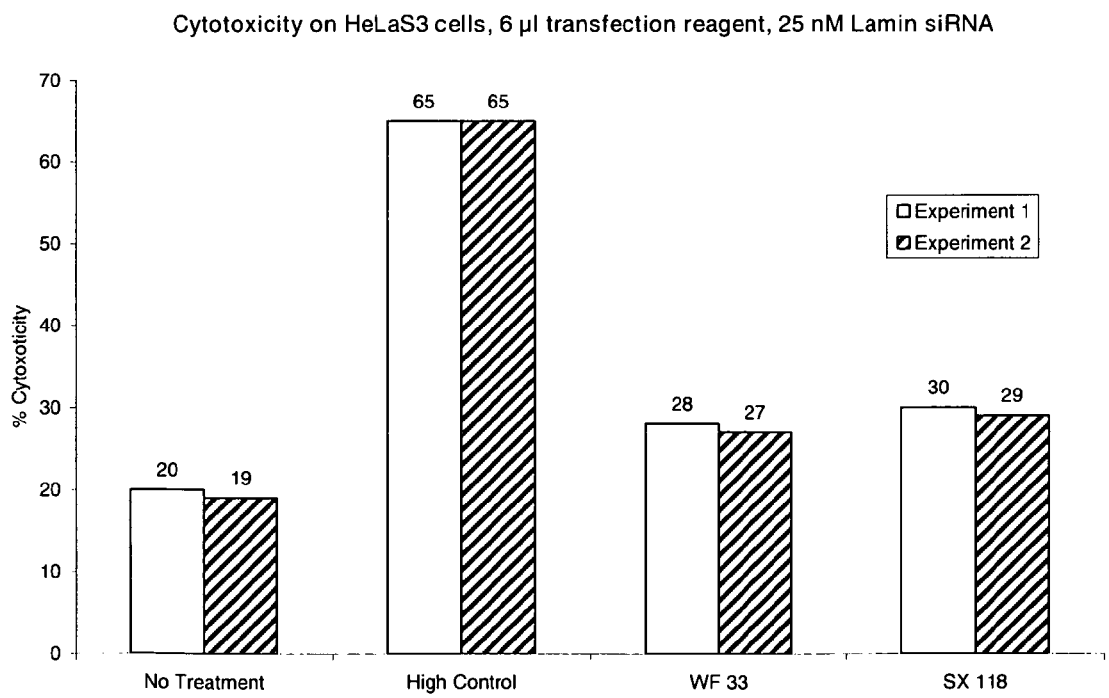
Figure 10A:
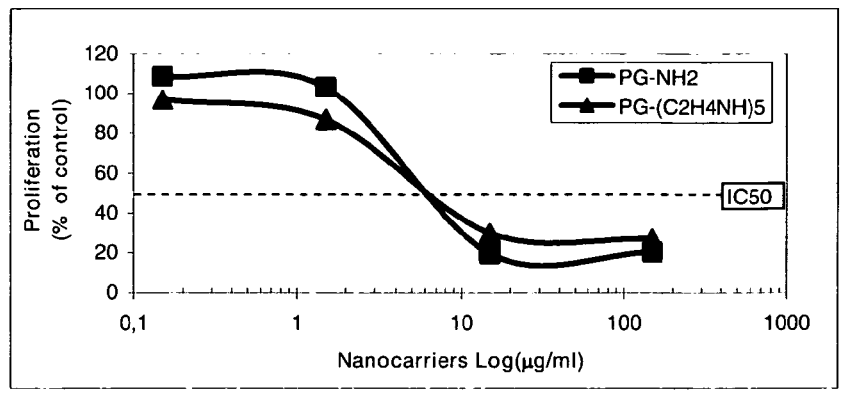
Figure 10B:
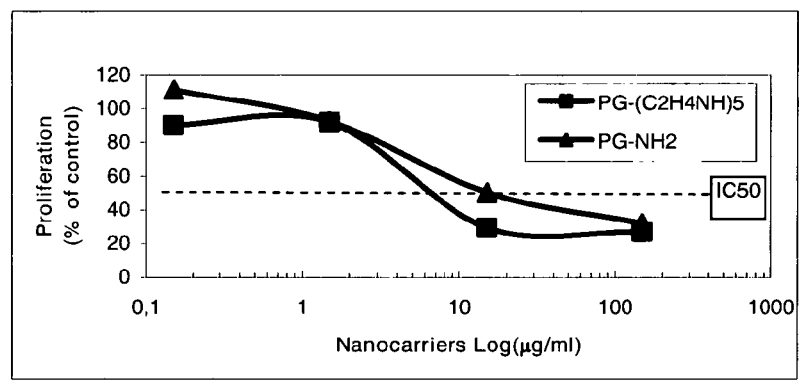
Figure 10C:
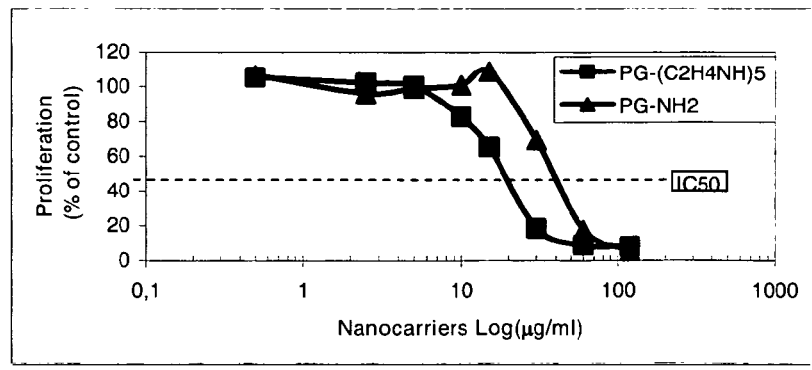
Figure 10D:
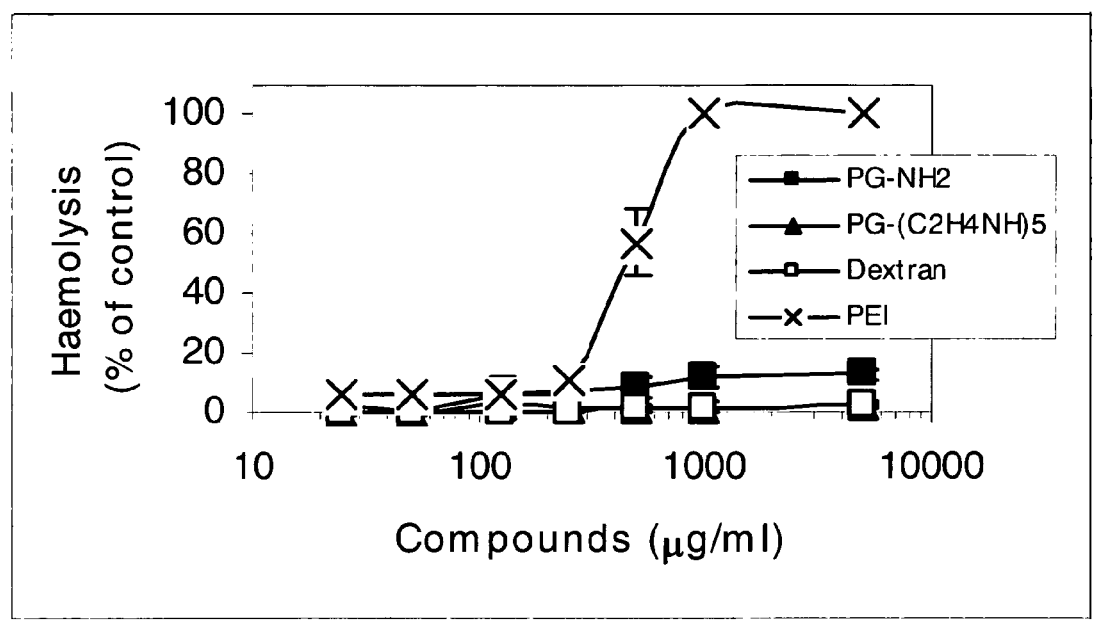
Figure 11A:
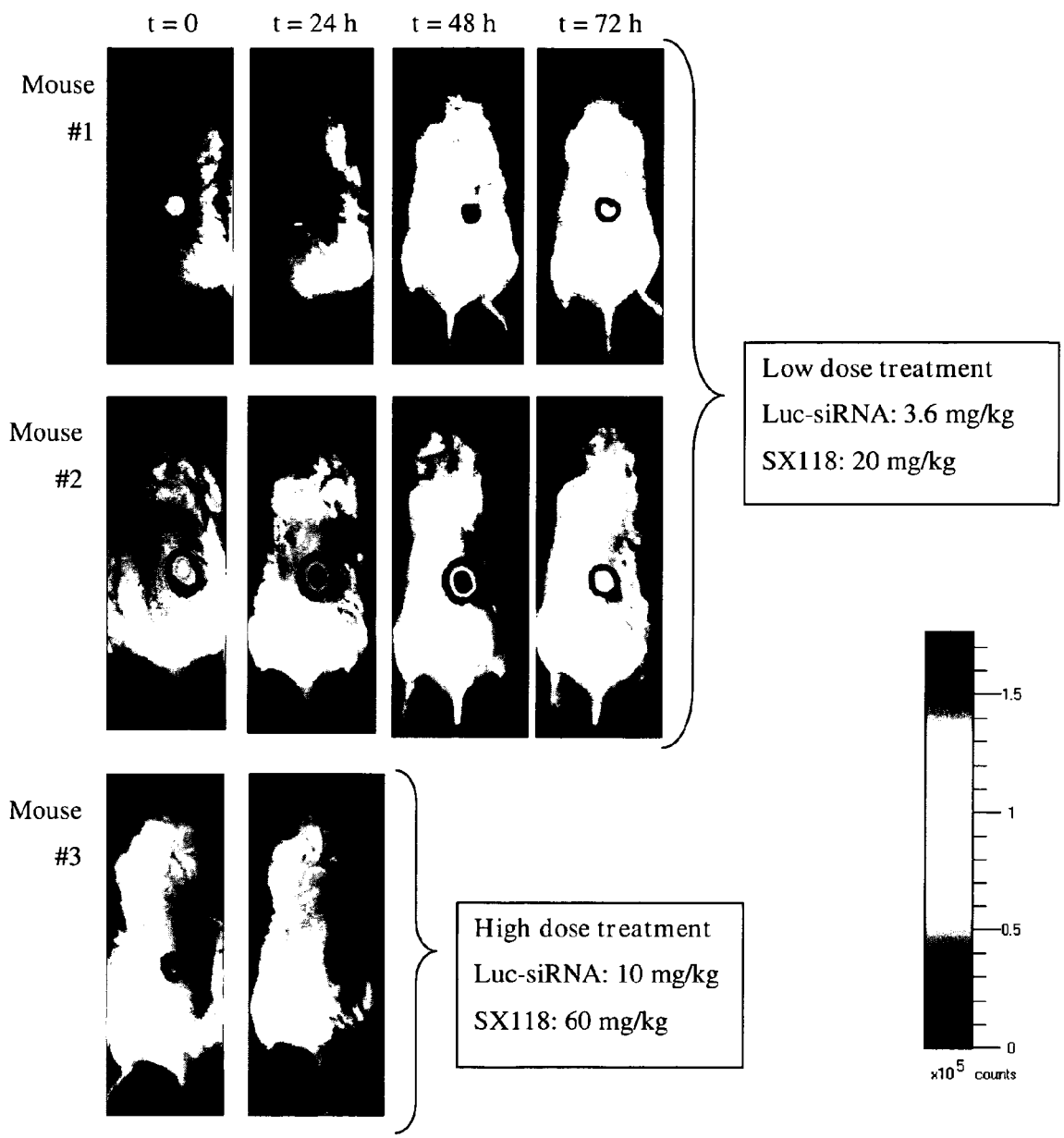
Figure 11B:
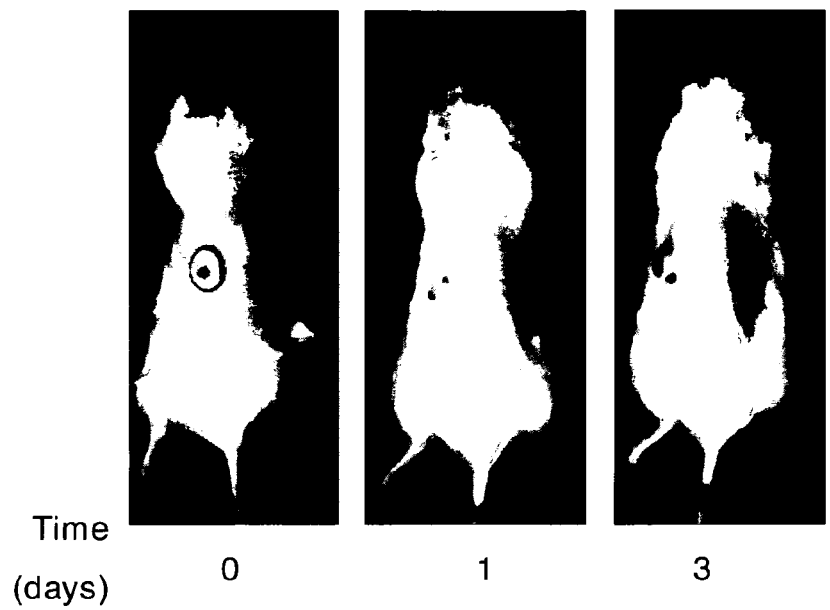
Figure 11C:
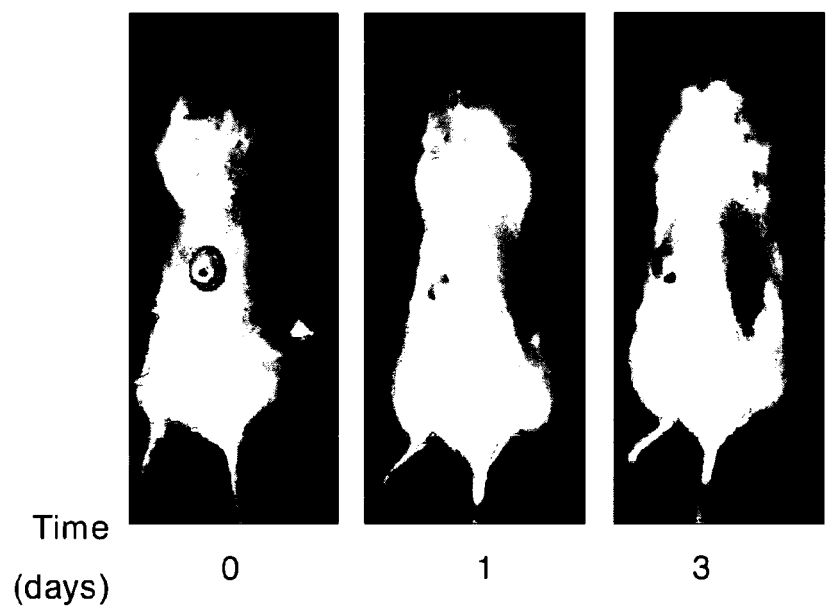
Figure 12A:
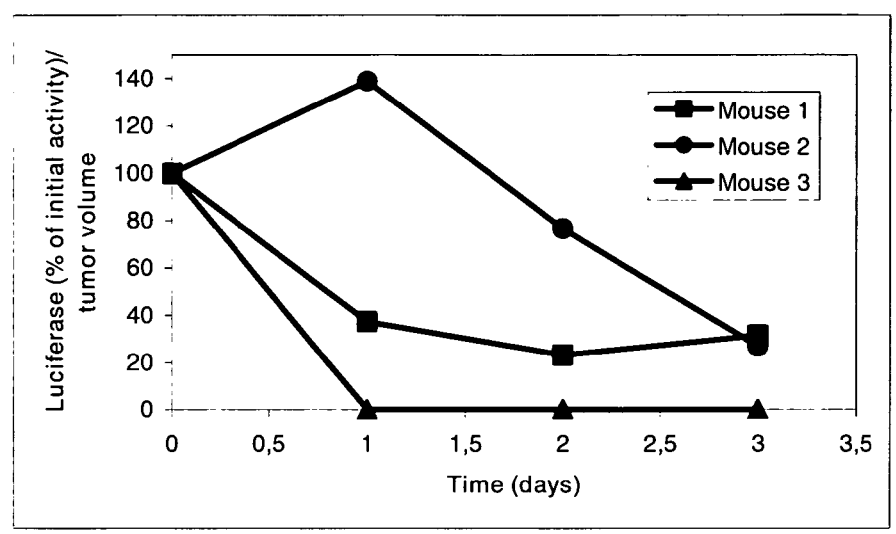
Figure 12B:
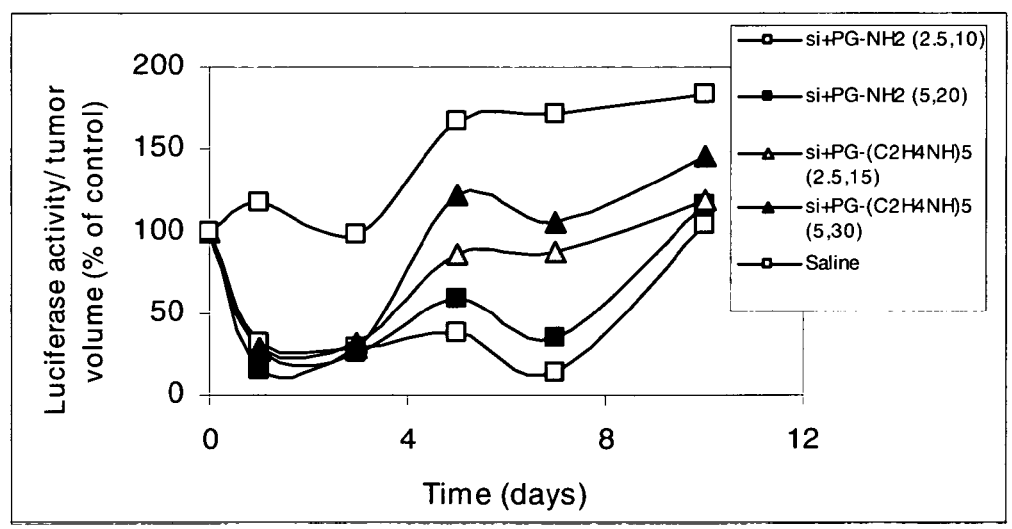
Figure 13A:
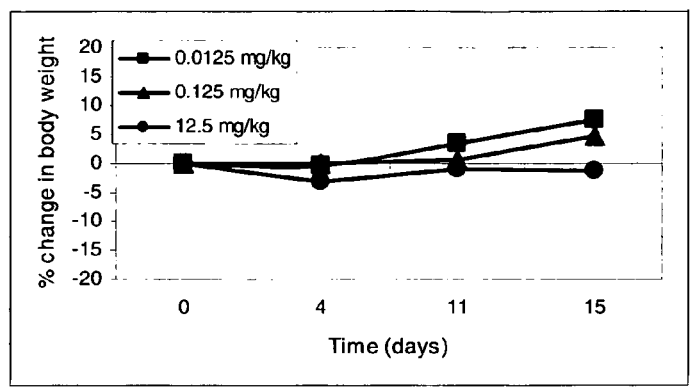
Figure 13B:
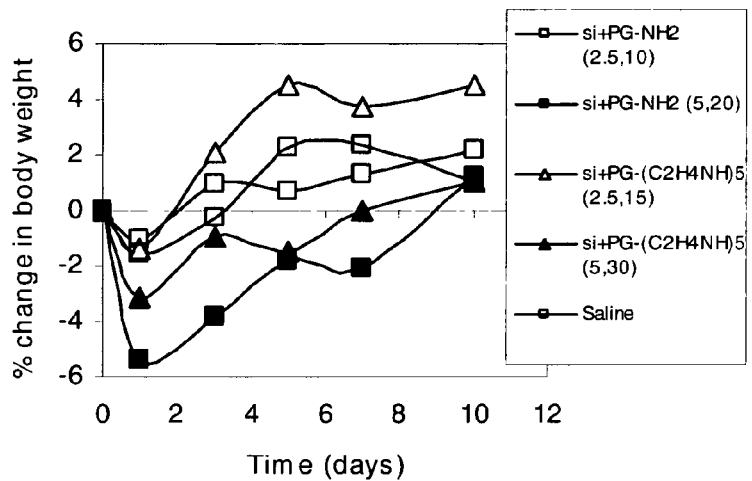
Figure 13C:
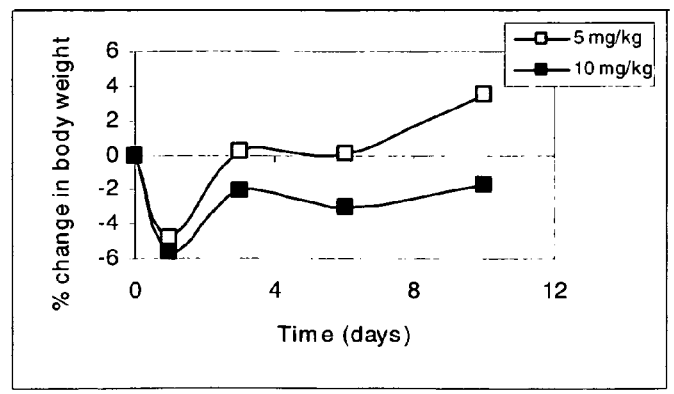
Figure 14:
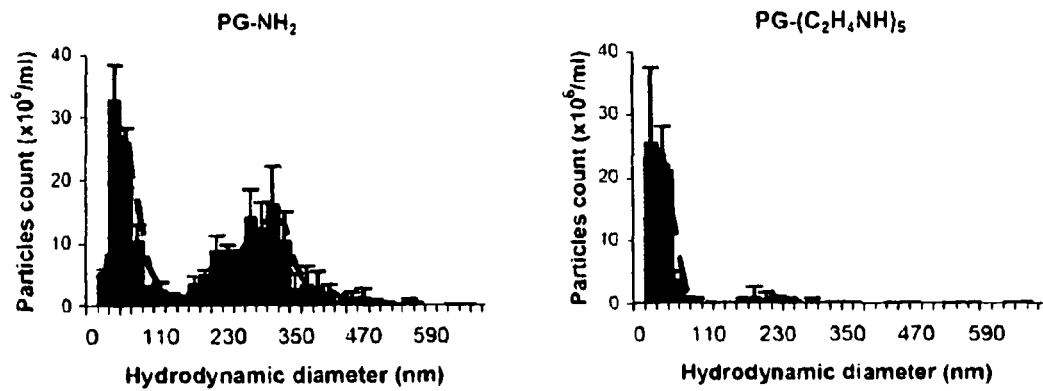
Figure 15:
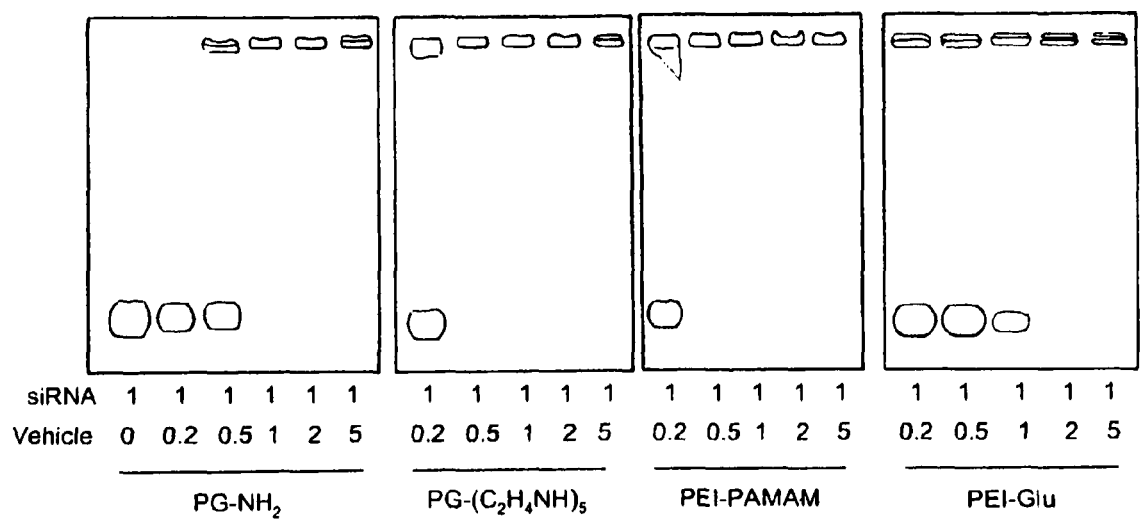
Figure 16:
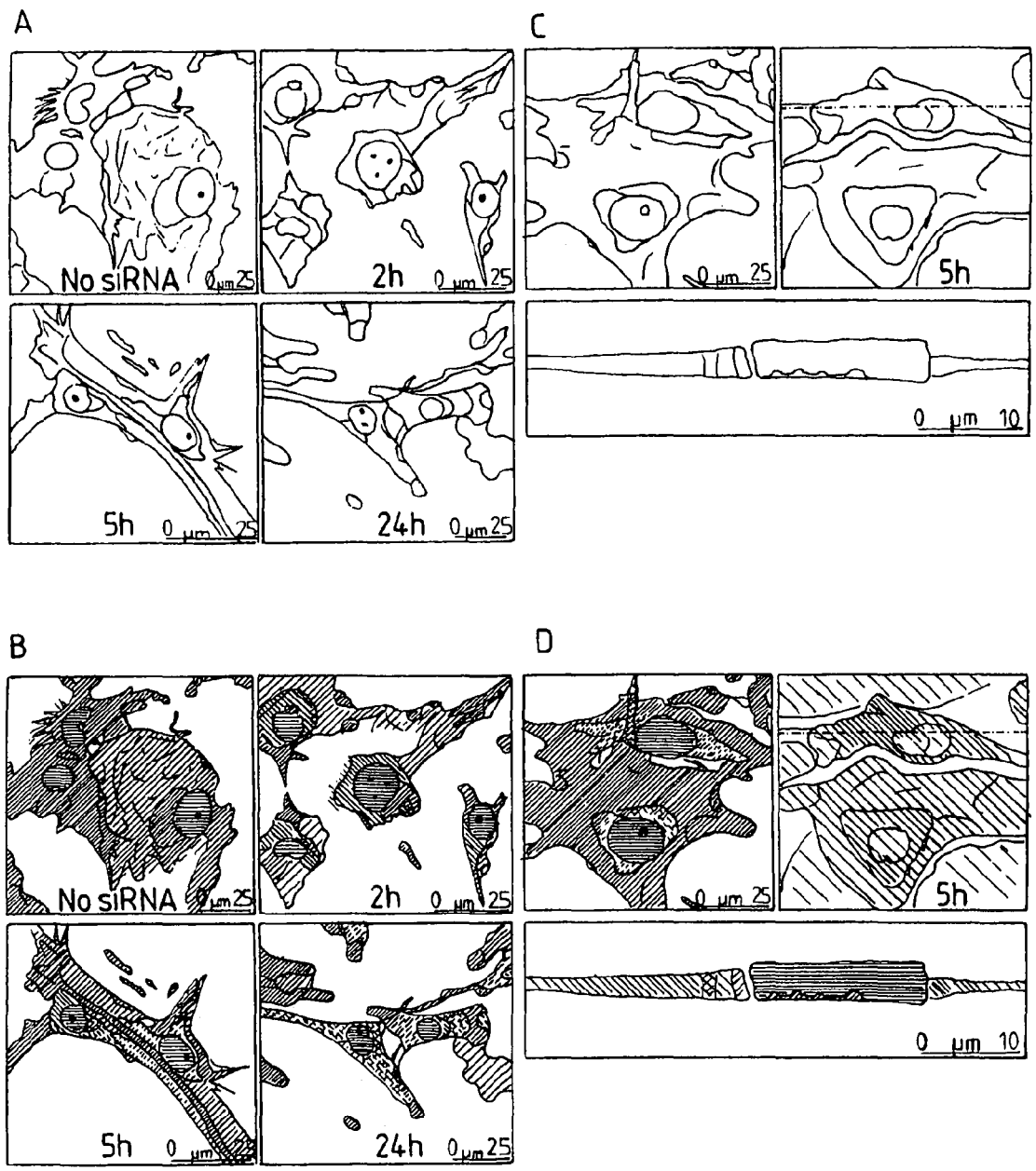
Figure 16:
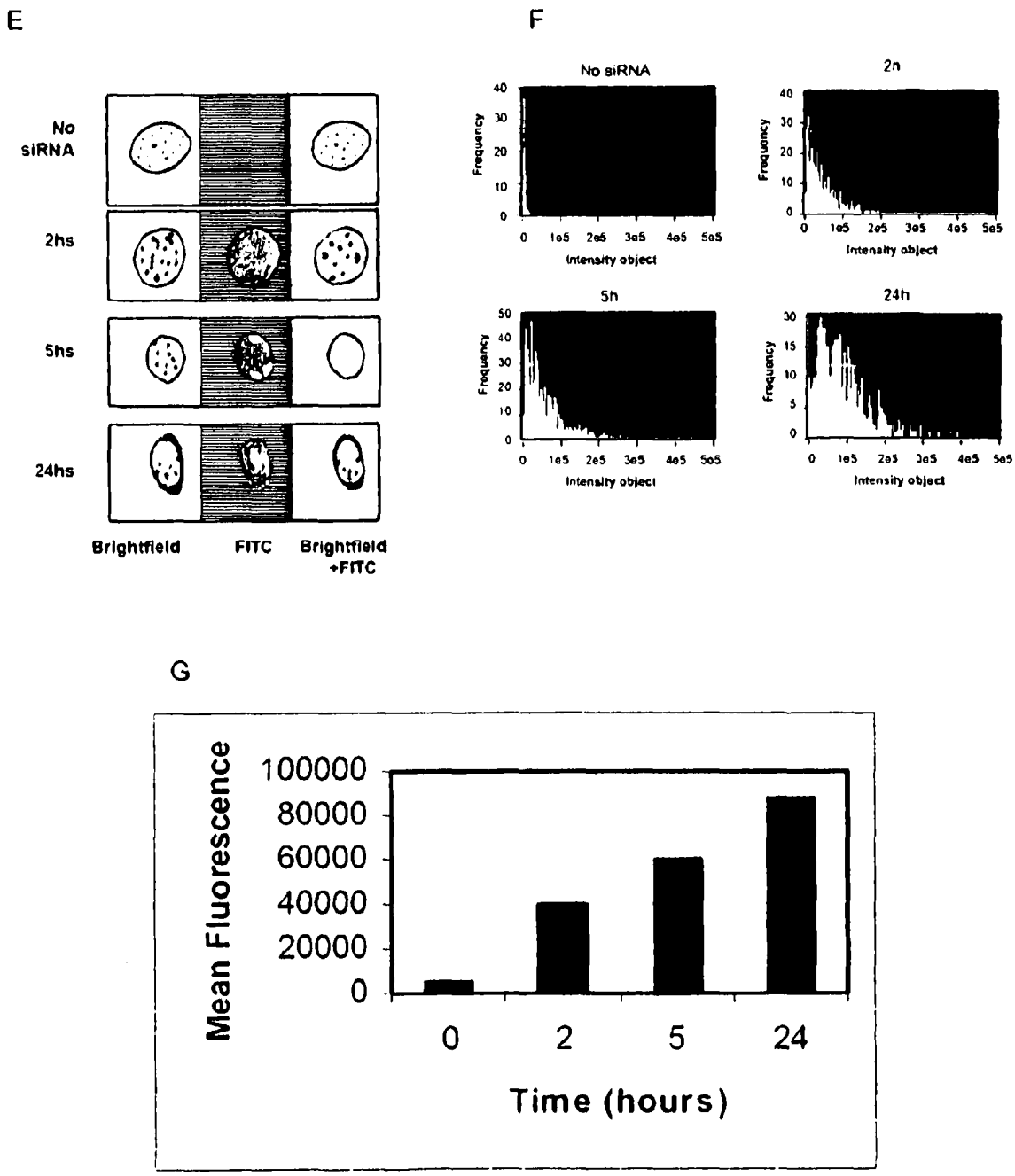
Figure 17:
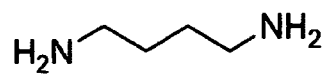
Figure 17:
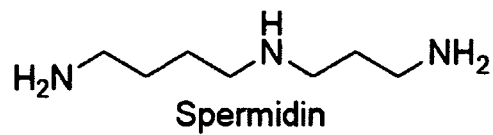
Figure 17:
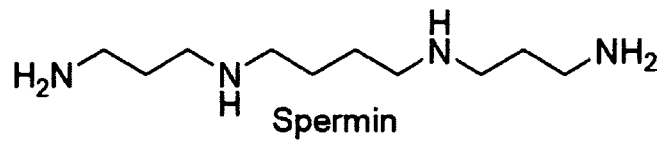
Figure 17:
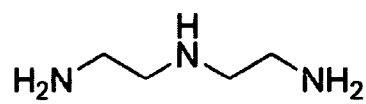
Figure 17:
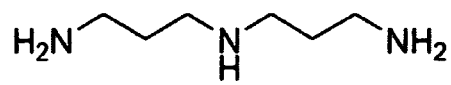
Figure 17:
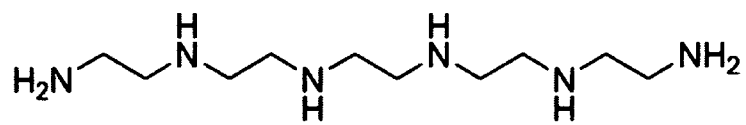

In the Figures:

FIG. 1 shows a cut-out of the polyglycerol core of a compound according to general formula (I), FIG. 2 shows a reaction scheme for the synthesis of different polyglyceryl ethyleneamine carbamates as examples of a compound according to formula (I), FIG. 3 shows a reaction scheme for the synthesis of different amino analogues of polyglycerol as further examples of compounds according to formula (I), FIG. 4 shows in vitro siRNA gene silencing efficiency of siRNA loaded PG-$(C_2H_4NH)_5$ (WF33) and PG-$NH_2$ (SX118) with respect to Lamin expression in HeLaS3 cells, FIG. 5 shows in vitro siRNA gene silencing efficiency of siRNA loaded PG-$(C_2H_4NH)_5$ (WF33) and PG-$NH_2$ (SX118) with respect to CDC2 expression in HeLaS3 cells, FIG. 6 shows in vitro siRNA gene silencing efficiency of siRNA loaded PG-$(C_2H_4NH)_5$ (WF33) and PG-$NH_2$ (SX118) with respect to MAPK2 expression in HeLaS3 cells, FIG. 7 shows in vitro siRNA gene silencing efficiency of siRNA loaded PG-$(C_2H_4NH)_5$ and PG-$NH_2$ with respect to luciferase expression in U87-Luc cells, FIG. 8 shows in vitro cytotoxicity of PG-$(C_2H_4NH)_5$ (WF33) and PG-$NH_2$ (SX118) on HeLaS3 cells, FIG. 9 shows in vitro cytotoxicity of PG-$(C_2H_4NH)_5$ (WF33) and PG-$NH_2$ (SX118) on HeLaS3 cells, FIG. 10A shows the cytotoxicity of PG-$NH_2$ and PG-$(C_2H_4NH)_5$ on SK-N-SH neuroblastoma cells, FIG. 10B shows the cytotoxicity of PG-$NH_2$ and PG-$(C_2H_4NH)_5$ on Kelly neuroblastoma cells, FIG. 10C shows the cytotoxicity of PG-$NH_2$ and PG-$(C_2H_4NH)_5$ on U87 human glioblastoma cells, FIG. 10D shows the results of a red blood cell lysis assay using PG-$NH_2$ and PG-$(C_2H_4NH)_5$, compared to positive (triton X and PEI) and negative (dextran) controls, FIG. 11A shows luciferase activities within generated tumors of mice at different measurement times as bioluminescence images, FIG. 11B shows representative bioluminescence images of a SCID mouse bearing a human U87-Luc glioblastoma tumor inoculated subcutaneously, that was treated intratumorally with low dose of luciferase siRNA-PG-$NH_2$, at different times, FIG. 11C shows the same representation as FIG. 11B, but in colour, FIG. 12A shows the luciferase activities of FIG. 11A as percent of the initial luciferase activity, FIG. 12B shows the luciferase silencing activity normalized to tumor volume plotted versus time of SCID mouse bearing a U87-Luc tumor treated intratumorally with luciferase siRNA-PG-$NH_2$ or luciferase siRNA-PG-$(C_2H_4NH)_5$, FIG. 13A shows body weight change of animals after treatment with different doses of SX 118, FIG. 13B shows body weight change of animals after intratumoral treatment with different doses of siRNA-PG-$NH_2$ or siRNA-PG-$(C_2H_4NH)_5$, FIG. 13C shows the results of a biocompatibility evaluation of intravenous administration of PG-$NH_2$ at two different concentrations into mice, presented as change in body weight following treatment vs. time, FIG. 14 shows the hydrodynamic diameter size distribution of PG-$NH_2$ and PG-$(C_2H_4NH)_5$, FIG. 15 shows the results of a gel mobility-shift assay of siRNA incubated with PG-$NH_2$, or PG-$(C_2H_4NH)_5$, PEI- PAMAM (i.e., poly(ethylene imine)-polyamidoamine) or PEI-Gluconolacton (i.e. poly(ethylene imine) gluconolacton) at several molar ratios, FIG. 16A shows confocal microscopy images (XY image plane) of fixed U87 cells transfected with Cy3-labeled anti-luciferase siRNA complexed with PG-$NH_2$, FIG. 16B shows the same representation as FIG. 16A, but in colour, FIG. 16C also shows confocal microscopy images (XZ image plane) of fixed U87 cells transfected with Cy3-labeled anti-luciferase siRNA complexed with PG-$NH_2$, FIG. 16D shows the same representation as FIG. 16C, but in colour, FIG. 16E shows brightfield and fluorescence images of live cells prepared in suspension as results obtained by an ImageStream multispectral imaging flow cytometer of U87 cells transfected with FITC-labeled anti-Luciferase siRNA complexed with PG-$NH_2$, FIG. 16F shows intracellular internalization histograms as analyzed flow cytometric results of the experiment of FIG. 16E, FIG. 16G shows levels of siRNA accumulated in the cells cytoplasm (mean fluorescence) as further flow cytometric results of the experiment of FIG. 16E, FIG. 17 shows the chemical structures of different natural polyamines, FIG. 18A shows two reaction schemes for the synthesis of nanocarriers by glycerol oxidation and amination and FIG. 18B shows a reaction scheme for the synthesis of nanocarriers by a Mitsunobu reaction.

FIG. 1 shows a cut-out of the polyglycerol core of a compound according to general formula (I). The grade of branching of the polyglycerol structure can differ from that depicted in FIG. 1. Also, the molecular mass of a polyglycerol core structure of the claimed invention can be equal to that shown in FIG. 1 or can be lower or higher. During synthesis of the compounds according to general formula (I), substitution reactions take place at free hydroxyl residues (—OH) of the polyglycerol structure. In the abbreviated structure

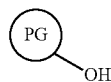

only a single hydroxyl group is indicated. However, this single hydroxyl group is to be understood as representative of all free hydroxyl groups being present in the polyglycerol.

FIGS. 2 and 3 showing reaction schemes will be explained in conjunction with examples 1 to 3.

FIGS. 4 to 7 showing siRNA silencing efficiencies of two siRNA loaded nanocarriers with respect to different protein expressions will be explained in the context of example 4.

FIGS. 8, 9 and 10A to 10D relating to cytotoxicity experiments will be explained in conjunction with example 5.

FIGS. 11 and 12 relating to an in vivo gene silencing experiment will be explained in conjunction with example 6.

FIG. 13 relating to body weight change of animals after treatment with a nanocarrier will be explained in conjunction with example 7.

Figure 18:
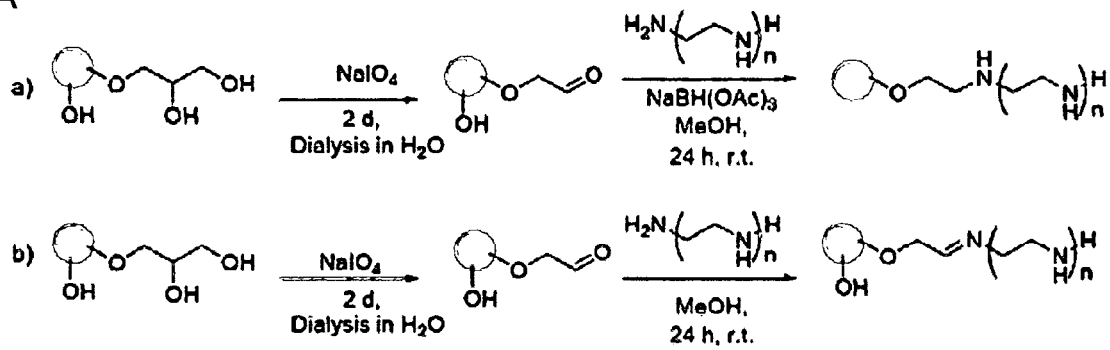
Figure 18:
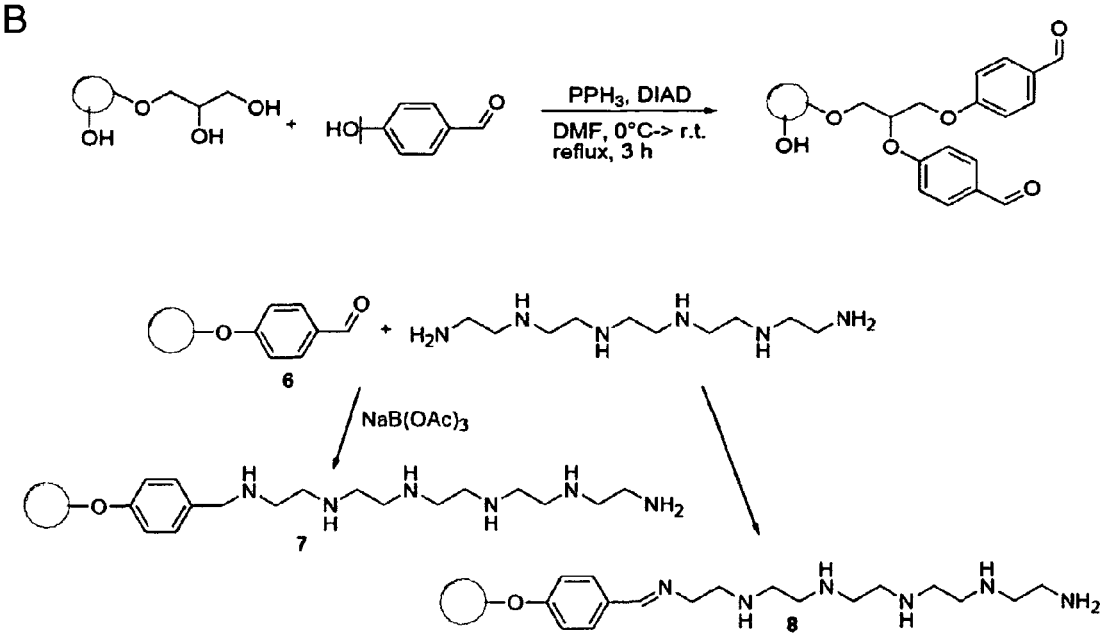

FIG. 14 will be explained in conjunction with Example 8.
FIG. 15 will be explained in conjunction with Example 9.
FIG. 16 will be explained in conjunction with Example 10.
FIGS. 17 and 18 will be explained in conjunction with Example 11.

Example 1

Synthesis of Polyglyceryl Ethyleneamine Carbamates

The synthesis of polyglyceryl ethyleneamine carbamates as examples of amine terminated polyglycerol (PG) compounds was carried out in a two-step protocol (see FIG. 2). In the first step, hyperbranched polyglycerol 1 (cf. also FIG. 1) was activated to phenyl polyglycerol carbonate 2. In the second step, this activated polyglycerol was reacted with amines of different chain length to form amine terminated polyglycerols 8. By this reaction pathway, it is possible to synthesize a library of different amine derivatives based on a PG core.

As an example of polyglyceryl ethyleneamine carbamates, the synthesis of polyglyceryl pentaethylenehexamine carbamate will be explained in more detail.

1a) Synthesis of phenyl polyglyceryl carbonate (carbonic acid phenylpolyglyceryl ester) 2

This reaction was performed under an inert gas atmosphere and exclusion of water. To absolute (abs.) pyridine (100 ml) in a three necked 500-ml flask with drop funnel, thermometer, and magnetic stirrer was added while stirring at 0° C. phenyl chloroformate 5 (19.6 ml, 24.4 g, 156 mmol, 1.2 equivalents (eq.)). On addition a white precipitate formed.

Subsequently, a solution of polyglycerol 1 (10.0 g, 135 mmol OH-groups) in abs. pyridine (80 ml) was added at 0° C. The mixture was stirred in the thawing cooling bath for 16 h. Then $H_2O$ and $CHCl_3$ were added until all solid was dissolved. The phases were separated and the organic layer was extracted three times with $CHCl_3$. The combined organic layers were dried over $MgSO_4$, concentrated in vacuo and dialysed in $CHCl_3$ to give a brown honey-like product.

Conversion: quantitative (quant.); yield: 92%; $^1$H-NMR (500 MHz, $CDCl_3$): δ=7.61-6.87 (Ar—H), 5.32-4.92 (functionalised secondary PG-groups), 4.76-4.10 (functionalised primary PG-groups), 4.05-3.06 (PG), 1.73 (PG-starter), 0.86 (PG-starter); $^{13}$C-NMR (125 MHz, $CDCl_3$): δ=153.5 (1-C), 151.1 (2-C), 129.6 (4-C/6-C), 126.2 (5-C), 121.1 (3-C/7-C); IR (KBr): ν=3125-2750, 1761, 1592, 1494, 1458, 1237, 1072, 1023, 913, 775, 727, 688 $cm^{-1}$.

1b) Synthesis of Polyglyceryl pentaethylenehexamine carbamate 7

A solution of phenyl polyglyceryl carbonate 5 (2.215 g, 11.15 mmol, 1 eq.) in p.a. pyridine (80 ml) was dropped over 2 h at 0° C. to an emulsion of pentaethylenehexamine 6 (25.92 g, 111.56 mmol, 10 eq.) and 4-(Dimethylamino)-pyridine (DMAP; 0.027 g, 0.2231 mmol, 0.01 eq.) in pyridine. The mixture was refluxed for 16 h and after cooling, concentrated in vacuo. After removal of pyridine residues in high vacuum, the raw product was dialyzed in methanol (MeOH) to give a brown honey-like product.

Conversion: 67%; yield: 73%; $^1$HNMR (250 MHz, $CD_3OD$): δ=4.40-3.03 (PG), 1.41 (PG-starter), 0.89 (PG-starter); $^{13}$CNMR (75 MHz, $D_2O$): δ=159.4 (CO), 81.2-59.4 (PG); IR (KBr): ν=3328, 2876, 2361, 1721, 1630, 1514, 1461, 1278, 1180, 1077 $cm^{-1}$.

$^1$HNMR (MeOD, 250 MHz): δ (ppm)=2.5-2.9 (m, H1-H9), 3.1-3.2 (H11), 3.3-3.9 (PG), 4.2-4.4 (H12).

$^{13}$CNMR (125 MHz, $CD_3OD$): δ=40.2-50.0 (pentaethylenehexamine), 52.9-80.0 (PG-backbone), 158.15 (CO).

Example 2

Synthesis of N,N,N'-trimethylethylenediamine terminated polyglycerol

The synthesis of N,N,N'-trimethylethylenediamine terminated Polyglycerol as another example of an amine terminated polyglycerol (PG) was also carried out in a two step protocol (see FIG. 3). In the first step, hyperbranched polyglycerol 1 (cf. also FIG. 1) was activated to polyglycerol mesylate (mesylpolyglycerol) 3. In the second step, this activated polygylcerol was reacted with N,N,N'-trimethylethylenediamine to form N,N,N'-trimethylethylenediamine terminated polyglycerol.

2a) Synthesis of mesylpolyglycerol 3

Polyglycerol 1 (10 g, 135 mmol OH-groups) in a three necked flask with a drop funnel, thermometer, and magnetic stirrer was dissolved in abs. pyridine (80 ml). The solution was cooled down to 0° C. by means of ice/NaCl bath. A solution of mesylchloride (12.5 ml, 18.6 g, 162.16 mmol, 1.2 eq.) in abs. pyridine was added in a drop wise pattern. The reaction mixture was stirred for 16 h in the thawing ice bath. Then ice was added and a dark brown solid precipitated. After decantation of liquid, the solid was washed with $H_2O$, dissolved and dialyzed in acetone for overnight to give a brown honey-like product (mesylpolyglycerol 3) at 85% yield. The product was characterized by $^1H$ and $^{13}C$ NMR and was in complete compliance with spectroscopic assignments.

2b) Synthesis of Polyglyceryl trimethylethylenediamine 10

To a solution of mesylpolyglycerol 3 (0.5 g, 1 eq.) in dimethylformamide (DMF), was added N,N,N'-Trimethylethylenediamine 9 (2.1 ml, 5 eq.) in a sealed tube. The reaction mixture was stirred for 72 h at 90° C. After removal of DMF by cryo-distillation, the condensed reaction mixture was dissolved in $CHCl_3$ and extracted three times with saturated $NaHCO_3$ solution. Organic phases were collected and dried over $MgSO_4$. After filtration and evaporation of $CHCl_3$, a brown semisolid paste like product was obtained. Dialysis of the crude product against MeOH for 48 h yielded amine terminated polyglycerol 10 at 80% yield. Product characterization was done by $^1H$ and $^{13}C$ NMR. Final product was found to be soluble in water, MeOH and DMF.

Example 3

Synthesis of Polyglycerylamines

Polyglycerylamines were synthesized by mesylation of PG hydroxyl groups, conversion into azides and subsequent reduction to amines (see FIG. 3).

3a) Synthesis of polyglycerylazide 12

In a 500 ml one-necked flask with reflux condenser and magnetic stirrer was dissolved O-mesylpolyglycerol 3 (14.74 g, 90.96 mmol OMs groups) in pro analysi (p.a.) DMF (150 ml) upon ultrasonification. After addition of $NaN_3$ (29.57 g, 454.8 mmol, 5 eq.), the resulting suspension was heated at 60° C. for 3 days behind a transparent security wall. After cooling, filtration delivered a reddish filtrate and a white residue of excess $NaN_3$. The filtrate was concentrated in vacuo at temperatures below 40° C. and only handled with plastic spatula to avoid the potentially explosive degradation of the polyazide. The remainder was dissolved in $CHCl_3$ and extracted four times with water. The organic phase was dried over $MgSO_4$ and concentrated in vacuo. To remove traces of DMF from the raw product an additional dialysis in $CHCl_3$ was performed.

Conversion: quant.; yield: 86%; $^1HNMR$ (400 MHz, $CDCl_3$): δ=4.23-2.87 (PG), 1.81 (PG-starter), 0.85 (PG-starter); $^{13}CNMR$ (100 MHz, $CDCl_3$): δ=81.9-67.5 (PG), 60.5 (functionalised secondary PG-groups), 51.5 (functionalised primary PG-groups); IR (KBr): ν=2873, 2361, 2102 (N3), 1457, 1273, 1122, 668 $cm^{-1}$.

3b) Synthesis of Polyglycerylamine 13

Polyglycerylazide 12 (16.50 g, 166.7 mmol $N_3$-groups) was dissolved in p.a. THF (150 ml) in a 500 ml one-necked flask. $H_2O$ (10 ml) and $PPh_3$ (43.67 g, 166.7 mmol, 1 eq.) were added and $N_2$ formation was observed. While stirring for 16 h, the amount of water in the reaction mixture was increased continuously by dropwise addition of $H_2O$ (140 ml) via drop funnel to avoid precipitation of the partially reduced product. The mixture was concentrated in vacuo to a smaller volume, $CHCl_3$ was added and the phases were separated using a separation funnel. The aqueous layer was extracted with $CHCl_3$ four times and then concentrated to dryness to deliver a brown honey-like product 13, which was dialysed in MeOH.

Conversion: 82%; yield: 90%; $^1HNMR$ (300 MHz, $CD_3OD$): δ=4.01-3.21 (PG), 3.31-2.40 (functionalised PG-groups); $^{13}CNMR$ (75 MHz, $CD_3OD$): δ=83.0-65.5 (PG), 55.5-43.6 (functionalised PG-groups); IR (KBr): ν=3354, 2874, 2362, 2338, 2103, 1576, 1473, 1338, 1104, 820, 668 $cm^{-1}$.

Example 4

Gene Transfection In Vitro

Polyglyceryl pentaethylenehexamine carbamate 7 (in the following referred to as WF 33 or PG-$(C_2H_4NH)_5$) and polyglyceryl amine 13 (in the following referred to as SX 118 or PG-$NH_2$) were found to be particularly efficient for gene transfection as will be described in detail in the following. The term "gene transfection" is to be understood as "transfection with a polynucleotide or oligonucleotide".

The polynucleotides or oligonucleotides used in these experiments are able to bind to mRNA of the examined genes and to act via RNA interference as gene silencer. In this context, "expression of proteins" is to be understood as gene transcription and subsequent translation of mRNA into proteins. Thus, if a protein expression is diminished or at least partially silenced, the production of said protein is reduced as compared to usual levels at the step of gene transcription or mRNA translation, in particular at the step of mRNA translation by siRNA gene silencing.

Transfection experiments were done in the HeLaS3 cell line with different proteins (Lamin, CDC2, MAPK2). For the sake of simplicity, the proteins will be partially named hereinafter like their encoding genes, although other names are also common for the examined proteins, like, e.g., CDK1 or CDC28A for the protein encoded by CDC2 (cell division cycle 2).

The results of the gene transfection efficiencies of PG-$(C_2H_4NH)_5$ (WF33) and PG-$NH_2$ (SX118) are shown in FIGS. 4 to 6. The results were compared to the control transfection reagent HiPerFect (Qiagen) which is the in vitro benchmark transfection reagent. PG-(C$_2$H$_4$NH)$_5$ and PG-NH$_2$ were found to be highly efficient and thus very well suited for transfection of HeLaS3 cells.

In a siRNA gene silencing experiment against expression of Lamin protein in HeLaS3 cells, the results of which experiment are shown in FIG. 4, a constant amount of 100 nM (nmol/l) siRNA was treated with 3 μl or 6 μl of different transfection reagents (siRNA carriers).

In FIG. 4, the first column shows the expression of the protein without any treatment (control experiment). The Lamin expression reached in this control experiment was set to 100%.

The second two columns of FIG. 4 show the expression of the protein after treatment with HiPerFect as transfection reagent. The next two columns show the expression of Lamin after treatment with PG-(C$_2$H$_4$NH)$_5$ as transfection reagent and the last two columns show the expression of Lamin after treatment with PG-NH$_2$ as transfection agent. In each case, unfilled columns represent results obtained with 3 μl transfection reagent and diagonally hatched columns represent results obtained with 6 μl transfection reagent. All transfection reagents were equally concentrated.

As can be seen from FIG. 4, at a concentration of 100 nM siRNA, treatment with siRNA loaded transfection agents PG-(C$_2$H$_4$NH)$_5$ and PG-NH$_2$ resulted in efficient silencing of Lamin expression (14 to 21% of usual expression) which was comparable to that of silencing achieved with HiPerFect (12 to 15% of usual expression).

FIG. 5 shows the results of a siRNA gene silencing experiment against expression of CDC2 protein in HeLaS3 cells. The same siRNA carriers or transfection reagents as in the experiment against Lamin expression were used. However, 6 μl of each transfection reagent were used in all experiments. On the other hand, different concentrations (25, 50 and 100 nM) of siRNA were tested.

In FIG. 5, the first column shows the expression of the protein without any treatment (control experiment). The CDC2 expression reached in this control experiment was set to 100%.

The second three columns of FIG. 5 show the expression of the protein after treatment with HiPerFect as transfection reagent. The next three columns show the expression of CDC2 after treatment with PG-(C$_2$H$_4$NH)$_5$ as transfection reagent and the last three columns show the expression of CDC2 after treatment with PG-NH$_2$ as transfection agent. In each case, unfilled columns represent results obtained with 100 nM siRNA, diagonally hatched columns represent results obtained with 50 nM siRNA and horizontally hatched columns represent results obtained with 25 nM siRNA.

Whereas CDC2 expression could be silenced with HiPerFect as transfection agent at all three siRNA concentrations chosen, silencing of CDC2 expression was more efficient at a siRNA concentration of 100 nM as compared to the other concentrations chosen in case of PG-(C$_2$H$_4$NH)$_5$ and PG-NH$_2$ as transfection reagents. Nonetheless, efficient silencing was possible with PG-(C$_2$H$_4$NH)$_5$ and PG-NH$_2$, though the extent of silencing was lower than that found with respect to Lamin expression (cf. FIG. 4).

FIG. 6 shows the results of a siRNA gene silencing experiment against expression of MAPK2 (Mitogen activated kinase 2) in HeLaS3 cells. The same siRNA carriers or transfection reagents as in the experiment against Lamin or CDC2 expression were used. Like in the experiment against CDC2 expression, 6 μl of each transfection reagent were used in all experiments and different concentrations (25, 50 and 100 nM) of siRNA were tested.

In FIG. 6, the first column shows the expression of the protein without any treatment (control experiment). The MAPK2 expression reached in this control experiment was set to 100%.

The second three columns of FIG. 6 show the expression of the protein after treatment with HiPerFect as transfection reagent. The next three columns show the expression of MAPK2 after treatment with PG-(C$_2$H$_4$NH)$_5$ as transfection reagent and the last three columns show the expression of MAPK2 after treatment with PG-NH$_2$ as transfection agent. In each case, unfilled columns represent results obtained with 100 nM siRNA, diagonally hatched columns represent results obtained with 50 nM siRNA and horizontally hatched columns represent results obtained with 25 nM siRNA.

MAPK2 expression could be silenced with HiPerFect as transfection agent at all three siRNA concentrations chosen. Silencing of MAPK2 expression was also particularly efficient at a siRNA concentration of 100 nM and use of PG-NH$_2$ as transfection reagent (20% of the usual expression). With PG-(C$_2$H$_4$NH)$_5$ as transfection reagent, 54% expression was the lowest value achieved at a siRNA concentration of 100 nM. At siRNA concentrations of 50 or 25 nM, silencing with PG-(C$_2$H$_4$NH)$_5$ as transfection reagent was not that efficient as compared to HiPerFect as transfection reagent. Also, a concentration of 25 nM siRNA seemed to be too low for efficient silencing of MAPK2 expression when PG-NH$_2$ was used as transfection agent (93% of the usual expression was still observed in this case).

In another experiment, silencing of luciferase gene by using PG-(C$_2$H$_4$NH)$_5$ and PG-NH$_2$ as transfection reagent (or nanocarrier for respective siRNA) was examined. For this experiment, siRNA of luciferase gene was entrapped into PG-(C$_2$H$_4$NH)$_5$ and PG-NH$_2$ and transfected into U87 luciferase-infected cells (U87-Luc). Cells were harvested 48 h later and lysed. Luciferase activity was measured using a luminometer.

In FIG. 7, luciferase activity (in percent of a negative control without any treatment) is plotted versus different concentrations (on a logarithmic scale) of PG-(C$_2$H$_4$NH)$_5$ and PG-NH$_2$ as nanocarriers comprising 100 nM luciferase siRNA. Thus, the silencing efficiency of PG-(C$_2$H$_4$NH)$_5$ and PG-NH$_2$ loaded with luciferase siRNA can be seen from FIG. 7.

Example 5

Cytotoxicity Profiling of PG-(C$_2$H$_4$NH)$_5$ and PG-NH$_2$

Since PG-(C$_2$H$_4$NH)$_5$ and PG-NH$_2$ were found to be efficient for transfection into HeLaS3 Cell lines and also showed higher silencing of luciferase gene, they were tested for their cytotoxicity behaviour. In both cases almost no cytotoxicity was observed in case of administering 3 μl transfection agents (cf. FIG. 8). However, the toxicity shows an increment with increasing dose of transfection agents as can be seen from experiments using 6 μl of the respective transfection agents (cf. FIG. 9).

In FIGS. 8 and 9, in each case the results of two independent measurements are depicted. Results of the first experiments are represented by unfilled columns and results of the second experiments are represented by diagonally hatched columns.

Results obtained with respect to "no treatment" are a negative control representing the normal rate of cytotoxicity observed in a cell culture due to usual biological processes, such as apoptosis.

"High control" refers to a positive control. 24 h after transfection of the cells, 40 µl of a 10% (w/v) Triton 100 solution were added to the medium of non-transfected cells. After incubation at 37° C. for 1 h, the supernatant was removed and centrifuged. 100 µl of the resulting supernatant was then subjected to the cytotoxicity assay (for details, see below).

Cytotoxicity of PG-($C_2H_4NH$)$_5$ and PG-$NH_2$ was also tested for SK-N-SH neuroblastoma, Kelly neuroblastoma and U87 glioblastoma cells. The cell lines were challenged with respective nanocarriers at serial concentrations. Cells were counted 72 h later, by XTT (tetrazolium hydroxide) reagent. The use of tetrazolium salts, such as MTT (3-(4,5-dimethylthiazol-2-yl)-2,5-diphenyltetrazolium bromide), is based on the fact that living cells reduce tetrazolium salts into colored formazan compounds.

The biochemical procedure is based on the activity of mitochondria enzymes which are inactivated shortly after cell death. This method was found to be very efficient in assessing the viability of cells. A colorimetric method based on the tetrazolium salt, XTT, was developed in 1988. Whilst the use of MTT produced a non-soluble formazan compound which necessitated dissolving the dye in order to measure it, the use of XTT produces a soluble dye and simplifies the procedure of measuring proliferation, and is, therefore, an excellent solution to the quantification of cells and their viability without using radioactive isotopes. This kit was developed to assay cell proliferation in reaction to different growth factors, cytokines, nutrient components and drugs.

Results are presented as % of the control (proliferation without any treatment) in FIGS. 10A to 10C.

FIG. 10A shows the cytotoxicity of PG-$NH_2$ and PG-($C_2H_4NH$)$_5$ on SK-N-SH neuroblastoma cells, FIG. 10B shows the cytotoxicity of PG-$NH_2$ and PG-($C_2H_4NH$)$_5$ on Kelly neuroblastoma cells and FIG. 10C shows the cytotoxicity of PG-$NH_2$ and PG-($C_2H_4NH$)$_5$ on U87 human glioblastoma cells. In each case, different concentrations of the dendritic nanocarriers PG-$NH_2$ and PG-($C_2H_4NH$)$_5$ were tested. As explained above, living cells were counted by XTT assay 72 h after adding nanocarriers. Results are presented as % of the control (proliferation without any treatment).

Both PG-($C_2H_4NH$)$_5$ and PG-$NH_2$ were not cytotoxic in a concentration of up to 10 µg/ml on the three tested cell lines. In this context, cytotoxicity of the nanocarriers is assumed to be given if the concentration needed for gene silencing is significantly higher than their $IC_{50}$ value.

Table 1 shows the silencing efficiency versus toxicity of PG-($C_2H_4NH$)$_5$ and PG-$NH_2$, on U87-Luc human glioblastoma cells obtained from that experiments, the results of which are depicted in FIG. 7 (for cytotoxicity experiments, see also example 5). These architectures demonstrated the best silencing efficiency and safety in U87-Luc cells and therefore were selected for examining in vivo cytotoxicity and gene silencing efficacy studies.

TABLE 1

Silencing efficiency of luciferase gene and cytotoxicity on U87-Luc human glioblastoma cells of PG—($C_2H_4NH$)$_5$ and PG—$NH_2$.

| Nanocarrier | 50% silencing | 70% silencing | $IC_{50}$ |
|---|---|---|---|
| PG—($C_2H_4NH$)$_5$ | 17 µg/ml | 30 µg/ml | 55 µg/ml |
| PG—$NH_2$ | 8 µg/ml | 12 µg/ml | 30 µg/ml |

As can be seen from Table 1, the concentration at which 50% of the examined cells were inhibited by PG-($C_2H_4NH$)$_5$ or PG-$NH_2$ (the $IC_{50}$ value) was 55 and 30 µg/ml respectively.

At almost half of this concentration, 70% silencing (silencing being defined as "1—expression") was achieved when using PG-($C_2H_4NH$)$_5$ as nanocarrier for siRNA of luciferase gene. With PG-$NH_2$ as according nanocarrier, 70% silencing was already achieved at an even lower concentration (12 µg/ml) with respect to U87-Luc cells.

In order to further evaluate the biocompatibility of the nanocarriers with red blood cells, a Red Blood Cells Lysis assay (Duncan, R., Ferruti, P., Sgouras, D., Tuboku-Metzger, A., Ranucci, E., and Bignotti, F. *J Drug Target*, 2:341-347, 1994) was performed.

Fresh blood was obtained from male wistar rats (~250 g) by cardiac puncture and collected in heparinized tubes. The erythrocytes were then washed 3-4 times with pre-chilled PBS, to finally make a red blood cell (RBC) solution of 2% w/w in PBS. Double strength solutions of the carriers tested were prepared and 100 µl plated into a 96 well plate. Negative controls were PBS (blank) and Dextran (MW ~70 000): positive controls were 1% w/v solution of Triton X100 (100% lysis) and poly(ethylene imine) (PEI). 100 µl of the 2% w/w RBC stock solution was added to each well and incubated for 1 hour at 37° C. Following centrifugation at 1000*g for 10 minutes at RT, the supernatant was drawn off and its absorbance measured at 550 nm using a microplate reader (Genios, TECAN). The results were then expressed as % of haemoglobin released relative to the positive control (Triton X100).

The results clearly show that at concentrations up to 1 mg/ml the dendrimers were not haemolytic in vitro (FIG. 10D). In detail, FIG. 10D shows the results of the Red Blood Cells Lysis assay. A rat red blood cells solution (2% w/v in PBS) was added to a previously prepared 96-wells plate containing the tested compounds at serial concentrations (■ PG-$NH_2$, ▲ PG-($C_2H_4NH$)$_5$, □ Dextran, x PEI). Following incubation at 37° C. for 1 hour and centrifugation, haemoglobin release was measured spectrophotometrically ($OD_{550}$), using PBS as a blank. Results are presented as % of the released hemoglobin produced by Triton X-100±standard deviation.

Summarizing, dendritic nanocarriers are non-toxic at the concentrations required for gene silencing in vitro.

Example 6

In Vivo Silencing the Luciferase Gene by siRNA

In order to demonstrate the potential of the novel siRNA-nanocarriers in cancer therapy, preliminary in vivo experiments were performed.

All animal procedures were performed in compliance with Tel Aviv University, Sackler School of Medicine guidelines and protocols approved by the Institutional Animal Care and Use Committee.

On the one hand, human glioblastoma U87-Luciferase cells ($10^6$ cells in 100 µl phosphate buffered saline (PBS)) were injected subcutaneously into SCID (Severe Combined Immunodeficiency) mice (male, 6 to 8 weeks old). Once the tumors grew to a volume of about 100 mm$^3$, 7 or 21 nmol (3.6 or 10 mg/kg) luciferase siRNA mixed together with 56 or 170 nmol (20 or 60 mg/kg) SX 118, respectively, were injected intratumorally (t=0). The tumor volume was measured daily with a caliper. The silencing efficiency of the luciferase siRNA encapsulated in the SX118 nanoparticle or nanocarrier was followed up by non-invasive intravital bioluminescence imaging system (Biospace Photon Imager) following luciferin injection intraperitoneally (50 mg/kg).

The luciferase activity of mice treated with different amounts of luciferase siRNA entrapped in SX118 was followed up by non-invasive intravital bioluminescence imaging for 3 days following treatment. Mice 1 and 2 were injected with 3.6 mg/kg luciferase siRNA entrapped in 20 mg/kg SX118; and mouse 3 was injected with 10 mg/kg luciferase siRNA entrapped in 60 mg/kg SX118.

FIG. 11A depicts luciferase activity within the generated tumor at different measurement times as bioluminescence images.

FIG. 12A represents results as % of the initial luciferase activity (before any treatment), normalized to tumor volume. Complete gene silencing was accomplished in vivo within 24 hours following treatment with the high dose luciferase siRNA-SX118 complex (mouse 3), while 80% silencing was achieved following treatment with the low dose complex (mice 1 and 2) as measured by photon flux bioluminescence.

On the other hand, SCID mice male aged 6-8 weeks (Harlan Laboratories Israel LTD) were anesthesized by ketamine (150 mg/kg) and xylazine (12 mg/kg) and inoculated subcutaneously (s.c.) with $1 \times 10^6$ U87-Luciferase cells.

Tumor progression was monitored by caliper measurement (width×length$^2$×0.52). Mice were imaged by bioluminescence imaging system (Biospace Photon Imager), following an intraperitoneal (i.p.) injection of luciferin (50 mg/kg). Photons were collected for a period of 15 minutes, images were obtained by Photonvision+ software (Biospace) and results analysis was performed by Molecular Vision software (Biospace).

Mice bearing 70 mm$^3$ tumors were injected intratumorally with luciferase siRNA-PGNH$_2$ and luciferase siRNA-PG (C$_2$H$_4$NH)$_5$ complexes at two different concentrations, siRNA alone or saline, as detailed in the table 2.

TABLE 2

Experimental Details of intratumoral injection.

|  | PG—NH$_2$ + siRNA | PG(C$_2$H$_4$NH)$_5$ + siRNA | siRNA alone | Saline |
|---|---|---|---|---|
| siRNA (mg/kg) | 2.5, 5 | 2.5, 5 | 2.5, 5 | — |
| Vehicle (mg/kg) | 10, 20 | 15, 30 | — | — |

Human glioblastoma U87-Luciferase cells were inoculated subcutaneously into SCID mice. Once tumors developed, anti-luciferase-siRNA complexed with PG-NH$_2$ or PG-(C$_2$H$_4$NH)$_5$ was injected intratumorally. Mice were administered with two injections of the different treatments, on day 0 and day 4. Animals were monitored 3 times a week for general health, body weight, tumor volume and luciferase activity following treatment.

A significant gene silencing (32% and 15%) was accomplished in vivo within 24 hours following treatment with luciferase siRNA complexed with PG-NH$_2$ (2.5 (low dose) and 5 mg/kg (high dose) siRNA complexed with 10 and 20 mg/kg PG-NH$_2$ respectively), as measured by photon flux bioluminescence (FIGS. 11B and 12B).

In detail, in FIGS. 12B and 13B black squares denote a high dose, and grey squares denote a low dose of anti-luciferase siRNA complexed with PG-NH$_2$. Further, black triangles denote a high dose, and grey triangles denote a low dose of anti-luciferase siRNA complexed with PG-(C$_2$H$_4$NH)$_5$. As a control, saline was injected to control mice (indicated by white squares). Mice received 2 injections, on day 0 and on day 4.

Low levels of luciferase activity were maintained for 3-4 days after a single dose of siRNA-nanocarrier, and even for 3 days more, following a second dose of the treatment on day 4. Similar results were obtained within 1-3 days following treatment with luciferase siRNA entrapped in the nanocarrier PG-(C$_2$H$_4$NH)$_5$. However, in this case, the silencing effect was not prolonged by a second dose at day 5 (FIG. 12, black and grey triangles). No significant weight loss occurred following two consecutive intratumoral injections of all complexes of dendritic vehicles and siRNA at two different doses to SCID mice (FIG. 13B).

Summarizing, intratumoral injection of PG-NH$_2$-siRNA and PG-(C$_2$H$_4$NH)$_5$-siRNA complexes leads to in vivo gene silencing.

Example 7

Biocompatibility of Intravenously Administered PG-NH$_2$ In Vivo

Further, preliminary in vivo biocompatibility tests for intravenous administration of PG-NH$_2$ (FIG. 13) were performed.

Firstly, mice were injected intravenously with increasing doses of SX 118 (0.0125, 0.125 and 12.5 mg/kg). Body weight, general physical condition and behaviour of the mice were monitored during 15 days following treatment. No significant change in the physical state or behaviour of the animals was observed during this period.

The percent of change in body weight 4, 11 and 15 days following treatment is plotted in FIG. 13A. Whereas at a high concentration of SX 118 injected, virtually no significant change in body weight can be seen after 15 days, an increase in body weight could be observed after 15 days in case of animals treated with low and medium doses of SX 118. Generally, an increase in body weight can be seen as an indication of a good physical state of an animal.

Secondly, PG-NH$_2$ (5 mg/kg (low dose) and 10 mg/kg (high dose)), without siRNA, was administered by injection into the tail vein of 6-8 weeks old male FVB mice (a commonly used mice strain). Animals were monitored daily for general health and changes in body weight during 14 days following treatment.

In FIG. 13C the percent change in the body weight of the mice is plotted. Black squares denote a high dose, and grey squares denote a low dose of PG-NH$_2$.

No significant change in the body weight of the mice was observed. General health and behaviour were also monitored and found to be suitable.

Summarizing, the synthetic protocols and biological experiments of the amine terminated PG herein disclosed reveal that such polymeric scaffolds hold high possibilities to transfect siRNA into the cellular matrix with appreciable biocompatibility. The polycationic architecture of these systems provides them with rapid cellular uptake and longer nuclear residence time.

Example 8

Determination of the Average Size by Dynamic Light Scattering (DLS)

The mean hydrodynamic diameter of the nanocarriers prepared according to examples 1 to 3 was evaluated using a real time particle analyzer (NanoSight LM20™) containing a solid-state, single mode laser diode (<20 mW, 655 nm) configured to launch a finely focused beam through a 500 µl sample chamber. PG-NH$_2$ and PG-(C$_2$H$_4$NH)$_5$ were dissolved in phosphate buffered saline (PBS) to a final concentrations of 1 mg/ml. The samples were then injected into the chamber by syringe and allowed to equilibrate to unit temperature (23° C.) for 30 seconds. The particles dynamics were visualized at 30 frames per second (fps) for 60 seconds at 640×480 resolution by the coupled charge device (CCD) camera. The paths the particles took under Brownian motion over time were analyzed using Nanoparticle Tracking Analysis (NTA) software. The diffusion coefficient and hence sphere equivalent hydrodynamic diameter of each particle was separately determined and the particle size distribution profiles were generated. Each sample was measured three times in triplicates, and the results represent the mean diameter.

The results can be seen from FIG. 14. In particular for $PG-NH_2$, two pronounced populations of differently sized particles can be observed.

Example 9

Polyplex Formation Study Between the Dendritic Nanocarriers and siRNA

For this and the following experiments, Fluorescein isothiocyanate (FITC)-labeled or Cyanine-3 (Cy3)-labeled anti-luciferase siRNA (5' GAU UAU GUC CGG UUA UGU AUU 3') and non-targeting siRNA purchased from Dharmacon were used. It is possible that the siRNA will be labeled with a certain marker and the dendritic polymer with a different marker.

The nanocarriers described in this and the following examples were prepared according to examples 1 to 3.

In order to establish the capability of the four tested dendritic nanocarriers to form a complex with siRNA, several amounts of dendrimers were incubated with an equal amount of siRNA and the efficacy of the complexes formation was analyzed by gel electrophoresis. The optimal ratio for the polyplex formation was studied by Electrophoretic Mobility Shift Assay (EMSA) as previously described (Kumar, P., Wu, H., McBride, J. L., Jung, K. E., Kim, M. H., Davidson, B. L., Lee, S. K., Shankar, P., and Manjunath, N, *Nature*, 448: 39-43, 2007). Briefly, 100 pmol of siRNA was incubated with $PG-NH_2$, $PG-(C_2H_4NH)_5$, PEI-PAMAM (i.e., poly(ethylene imine)-polyamidoamine) or PEI-Gluconolacton (i.e. poly (ethylene imine) gluconolacton) at 5:1, 2:1, 1:1, 1:2 and 1:5 molar ratios of siRNA to carrier, for 15 minutes at room temperature. Mobility of free or nanocarrier-complexed siRNA was then analyzed by agarose-gel electrophoresis.

The results of an according electrophoresis mobility shift assay can be seen from FIG. 15. All four nanocarriers were able to bind siRNA and neutralize its negative charge in a dose-dependent manner, as shown by an electrophoretic mobility shift assay. No significant differences between the ability of the four tested cationic carrier systems to encapsulate the siRNA were detected.

Example 10

Intracellular Trafficking of siRNA-PG-$NH_2$ Complex by Confocal Microscopy and by ImageStream Multispectral Imaging Flow Cytometer U87 human glioblastoma and human embryonic kidney 293T (HEK 293T) used in this and the following experiments were obtained from the American Type Culture Collection (ATCC). Cells were cultured in Dulbecco's modified Eagle's medium (DMEM) supplemented with 10% fetal bovine serum (FBS), 100 μg/ml Penicillin, 100 U/ml Streptomycin, 12.5 U/ml Nystatin and 2 mM L-glutamine (Biological Industries, Israel). Cells were grown at 37° C. in 5% $CO_2$.

For establishment of luciferase-infected U87 human glioblastoma cell line, HEK 293T cells were co-transfected with pLBLuc and the compatible packaging plasmids (pMD.G.VSVG and pGag-pol.gpt). Forty eight hours following transfection, the pLB-Luc retroviral particles containing supernatant were collected. U87 cells were infected with the retroviral particles media, and 48 hours following the infection, luciferase positive cells were selected by hygromycin resistance.

U87-Luc cells were plated at $2 \times 10^6$ cells/6 cm culture plate in Dulbecco's Modified Eagle Medium (DMEM), supplemented with 10% fetal bovine serum (FBS) for 24 hours. (FITC)-labeled Luciferase siRNA (100 nM) was mixed with PG-$NH_2$ (20 μg/ml) in serum free medium, incubated for 20 minutes at room temperature, and then added to the cells. Several time points following treatment with siRNA-PG-$NH_2$ complex (0, 2, 5 and 24 hours) cells were harvested, resuspended in 100 μl PBS, and analyzed by ImageStream multispectral imaging flow cytometer (Amnis Corp.). The platform produces high resolution brightfield, and fluorescence images of live cells prepared in suspension at rates up to 100 cells per second. The IDEAS™ analysis software quantifies over 200 morphometric and photometric parameters for each cell based on its imagery.

Following chemical characterization, the ability of Cy3-labeled anti-luciferase siRNA entrapped in PG-$NH_2$ to internalize into human glioblastoma cells was evaluated. U87 cells were incubated with the siRNA-PG-$NH_2$ 2, 5 and 24 hours following transfections. Cells were fixed, permeabilized, stained and analyzed by confocal microscopy.

In detail, U87-Luc cells were plated at 100,000 cells/well onto cover slides on 24-well culture plates in DMEM, supplemented with 10% fetal bovine serum (FBS) for 24 hours. Luciferase siRNA (100 nM) was mixed with PG-$NH_2$ (20 μg/ml) in serum free medium, incubated for 20 minutes at room temperature, and then added to the cells. U87 cells were incubated with siRNA-PG-$NH_2$ complex for 2, 5 and 24 hours or in the absence of siRNA, then washed several times with cold PBS, fixed with 4% paraformaldehyde (15 min, room temperature (RT)) and washed with PBS again. Actin filaments were labeled using phalloidin-FITC conjugate (25 μg/ml, 40 minutes at RT), nuclei were labeled using Hoechst staining (1 μg/ml, minutes at RT) and cover glasses were then mounted with Antifade® mounting media. Cellular uptake and internalization were monitored utilizing a Leica TCS SP5 confocal imaging system. All images were taken using a multi-track channel acquisition to prevent emission crosstalk between fluorescent dyes.

Thus, U87 cells were transfected with Cy3-labeled anti-luciferase siRNA encapsulated in PG-$NH_2$. The cells were fixed at the indicated time points following transfection, and analyzed by confocal microscopy (Leica TCS SP5). Following 2 hours incubation, siRNA was already detected inside the cells, accumulated mostly in the cytoplasm, as observed in the single plane image (FIG. 16A, 2 hours). FIG. 16A depicts single XY plane imaging of the siRNA (red) cytoplasmic accumulation, at the indicated times following transfection. Cells were stained with FITC-phalloidin (green) for actin filaments and DAPI (blue) for nuclei. The amount of siRNA accumulated inside the cells was significantly higher 3 hours later, and even more, the day after the transfection (FIG. 16A, 5 hours and 24 hours respectively). To evaluate the siRNA cellular localization and eliminate optical artefacts, an X, Z slice was captured and analyzed (FIG. 16C, lower panel). FIG. 16C shows XZ image slice (lower panel) of a cell fixed 5 hours following siRNA-PG-NH$_2$ transfection (upper panel) revealed similar siRNA, actin filaments and nuclei focal plane localization. Scale bars represent 25 µm and 10 µm for the XZ image slice. siRNA was located at the same focal plane as actin (stained by the FITC-labeled phalloidin), confirming its intracellular uptake.

Further examination of the cellular internalization of siRNA encapsulated in PG-NH$_2$ was performed by ImageStream multispectral imaging flow cytometer. Live cells were monitored different times following transfection, using FITC-labeled siRNA and Cy3-labeled phalloidin (red) for actin filaments, and siRNA intracellular uptake was monitored in live cells, at the indicated times following transfection (FIGS. 16E, 16F and 16G). PG-NH$_2$ was capable of delivering the siRNA into U87 cells as demonstrated by increasing levels of fluorescence measured inside the cells 2, 5 and 24 hours following transfection.

Summarizing, dendritic nanocarriers entrap siRNA and deliver it into human glioblastoma cells in vitro.

Example 11

Further Dendritic Nanocarriers

FIG. 17 shows the chemical structures of the natural polyamines putrescine, spermidine, spermine and its analogues diethylenetriamine, bis(3-aminopropylamine) and pentaethylenhexamine. These polyamines can also be used to modify polyglycerol in order to produce nanocarriers according to the invention. The synthesis can be generally done as described above, particularly with respect to examples 1 to 3. However, alternative reaction methods are possible.

In FIG. 18A and FIG. 18B such alternative methods are schematically depicted. Thus, FIG. 18A shows a glycol oxidation of polyglycerol and reductive amination (reaction a) and a glycol oxidation and formation of a Schiff base (reaction b), both ways leading to nanocarriers according to the invention. "r.t." stands for room temperature.

FIG. 18B shows the reaction scheme of a synthesis of pH cleavable systems through Mitsunobu reaction.

The invention claimed is:
1. A compound suited as an entity carrier, having the general formula (I)

with
PG denoting a linear or branched polyglycerol core,
X being

and being covalently bound to a carbon atom of the polyglycerol core, wherein the polyglycerol core carries a plurality of groups of X, such that at least 50% of the free hydroxyl groups of the polyglycerol core are substituted by groups of X,
R$^1$ being a methyl residue, and
R$^{2'}$ being an N-dimethyl ethyl amine residue.

2. A compound suited as an entity carrier, having the general formula (I)

with
PG denoting a linear or branched polyglycerol core,
X being

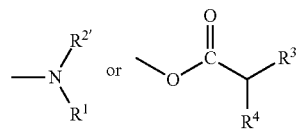

and being covalently bound to a carbon atom of the polyglycerol core, wherein the polyglycerol core carries a plurality of groups of X, such that at least 50% of the free hydroxyl groups of the polyglycerol core are substituted by groups of X,
R$^1$ being H, linear or branched C$_1$-C$_{10}$-Alkyl, which may be substituted and/or interrupted by one or more oxygen, sulfur, and/or nitrogen atoms, or R$^3$,
R$^{2'}$ being linear or branched C$_1$-C$_{10}$-Alkyl, which may be substituted and/or interrupted by one or more oxygen, sulfur, and/or nitrogen atoms, or R$^3$,
R$^3$ being

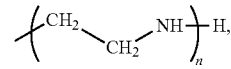

R$^4$ being H or C$_1$-C$_4$-Alkyl, which may be substituted and/or interrupted by one or more oxygen, sulfur, and/or nitrogen atoms, and
n being 1 to 100,
wherein R$^1$ and R$^2$ cannot simultaneously be an ethyl residue, characterized in that in that the compound bears at least one functional group of the general formula

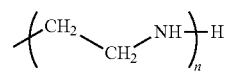

wherein residues R$^3$ and R$^4$ have the above-defined meanings.

3. Nanocarrier system comprising a compound according to claim 2 and at least one entity to be carried by and bound to said compound in a covalent, ionic or complexed manner, wherein said entity is chosen from the group comprising nucleotides, nucleosides, linear or circular single or double stranded oligonucleotides, oligomeric molecules comprising at least one nucleoside, small pharmacologically active molecules having a molecular mass of not more than 800 g/mol, amino acids, peptides, and metal ions.

4. A nanocarrier system according to claim 3, characterized in that all of the free hydroxyl groups of the polyglycerol core are substituted by groups of the type X.

5. A nanocarrier system comprising a compound according to claim 1 and at least one entity to be carried by and bound to said compound in a covalent, ionic or complexed manner, wherein said entity is chosen from the group comprising nucleotides, nucleosides, linear or circular single or double stranded oligonucleotides, oligomeric molecules comprising at least one nucleoside, small pharmacologically active molecules having a molecular mass of not more than 800 g/mol amino acids peptides and metal ions.

6. Nanocarrier system, comprising at least one nanocarrier being a compound according to claim 1,
at least one entity to be carried by and bound to said nanocarrier in a covalent, ionic or complexed manner, wherein said entity is chosen from the group comprising nucleotides, nucleosides, linear or circular single or double stranded oligonucleotides, oligomeric molecules comprising at least one nucleoside, small pharmacologically active molecules having a molecular mass of not more than 800 g/mol, amino acids, peptides, and metal ions,
with the provision that the entity does not comprise a double stranded circular and covalently closed nucleic acid having a length of more than 1000 bases or base pairs, preferably of more than 500 bases or base pairs.

7. A nanocarrier system according to claim 6, characterized in that the entity is a ribonucleic oligonucleotide.

8. A nanocarrier system according to claim 7, characterized in that the ribonucleic oligonucleotide has a length of 10 to 40 bases.

9. A pharmaceutical composition comprising the compound of claim 2, the composition being for use as a carrier for an entity, wherein the entity is chosen from the group comprising nucleotides, nucleosides, linear or circular single or double stranded oligonucleotides, oligomeric molecules comprising at least one nucleoside, small pharmacologically active molecules having a molecular of mass of not more than 800 g/mol, amino acids, peptides, and metal ions, with the provision that the entity does not comprise a double stranded circular and covalently closed nucleic acid having a length of more than 1000 bases or base pairs, preferably of more than 500 bases or base pairs.

10. A method of transporting an entity into at least one human cell selected from the group consisting of a HeLa cell a U87 glioblastoma cell an SK-N-SH neuroblastoma cell and a Kelly neuroblastoma cell, the method comprising contacting the cell with a nanocarrier system according to claim 3.

11. A method of transporting an entity into at least one human cell selected from the group consisting of a HeLa cell, a U87 glioblastoma cell, an SK-N-SH neuroblastoma cell and a Kelly neuroblastoma cell, the method comprising contacting the cell with a nanocarrier system according to claim 6, with the provision that the entity does not comprise a double stranded circular and covalently closed nucleic acid having a length of more than 1000 bases or base pairs, preferably of more than 500 bases or base pairs.

12. Kit for performing transfection reactions, comprising a compound according to claim 2 in any suited formulation.

13. Kit for performing transfection reactions, comprising a nanocarrier system according to claim 3 in any suited formulation.

14. Kit for performing transfection reactions, comprising a nanocarrier system according to claim 6 in any suited formulation.

15. A method of silencing a gene in vitro, ex vivo, in situ or in vivo, characterized by applying a nanocarrier system according to claim 6 into at least one human cell selected from the group consisting of a HeLa cell, a U87 glioblastoma cell, an SK-N-SH neuroblastoma cell and a Kelly neuroblastoma cell, wherein the entity is a ribonucleic oligonucleotide.

16. A method according to claim 15, characterized in that the gene to be silenced is a tumor related gene.

17. A method for the treatment of cancer, said cancer being selected from the group consisting of neuroblastoma and glioblastoma, characterized by administering a nanocarrier system according to claim 3 to at least one human being.

18. A method according to claim 17, characterized in that the treatment of cancer is performed as combination treatment by a combined administering of a known anti-cancer or anti-angiogenic drug.

19. A method for the treatment of cancer, said cancer being selected from the group consisting of neuroblastoma and glioblastoma, characterized by administering a nanocarrier system according to claim 6 to at least one human being.

20. A method according to claim 19, characterized in that the treatment of cancer is performed as combination treatment by a combined administering of a known anti-cancer or anti-angiogenic drug.

21. A method for the treatment of cancer, said cancer being selected from the group consisting of neuroblastoma and glioblastoma, characterized by administering to at least one animal or human being a nanocarrier system comprising: at least one nanocarrier being a compound according to claim 1,
at least one entity to be carried by and bound to said nanocarrier in a covalent, ionic or complexed manner, wherein said entity is chosen from the group comprising nucleotides, nucleosides, linear or circular single or double stranded oligonucleotides, oligomeric molecules comprising at least one nucleoside, small pharmacologically active molecules having a molecular mass of not more than 800 g/mol, amino acids, peptides, and metal ions.

22. A method according to claim 21, characterized in that the treatment of cancer is performed as combination treatment by a combined administering of a known anti-cancer or anti-angiogenic drug.

23. A compound suited as an entity carrier, having the general formula (I)

(I)

with
PG denoting a linear or branched polyglycerol core,
X being

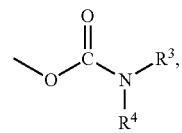

and being covalently bound to a carbon atom of the polyglycerol core, wherein the polyglycerol core carries a plurality of groups of X, such that at least 50% of the free hydroxyl groups of the polyglycerol core are substituted by groups of X,
$R^3$ being

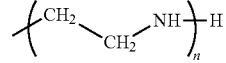

$R^4$ being H, and
n being 1 to 100.

24. A compound suited as an entity carrier, having the general formula (I)

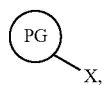  (I)

with
PG denoting a linear or branched polyglycerol core,
X being

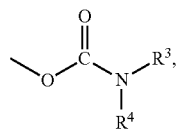

and being covalently bound to a carbon atom of the polyglycerol core, wherein the polyglycerol core carries a plurality of groups of X, such that at least 50% of the free hydroxyl groups of the polyglycerol core are substituted by groups of X, $R^3$ being

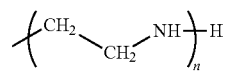

$R^4$ being H or $C_1$-$C_4$-Alkyl, which may be substituted and/or interrupted by one or more oxygen, sulfur, and/or nitrogen atoms, and n being 1 to 100.

* * * * *